United States Patent [19]
DelVecchio et al.

[11] Patent Number: 5,595,871
[45] Date of Patent: Jan. 21, 1997

[54] DETECTION AND PREVENTION OF MYCOPLASMA HOMINIS INFECTION

[75] Inventors: Vito G. DelVecchio, Scranton; Gary L. Gallia, Philadelphia, both of Pa.; Ferne K. McCleskey, San Antonio, Tex.

[73] Assignees: University of Scranton, Scranton, Pa.; Research Corporation Technologies, Inc., Tucson, Ariz.

[21] Appl. No.: 112,816

[22] Filed: Aug. 25, 1993

[51] Int. Cl.⁶ .............................. C12Q 1/68; C12P 19/34; C07H 21/04
[52] U.S. Cl. ..................... 435/6; 935/8; 935/77; 935/78; 435/91.2; 435/91.5; 435/172.3; 435/252.3; 435/320.1; 536/23.1; 536/24.32; 536/24.33
[58] Field of Search .............................. 435/6, 91.2, 91.1, 435/91.31, 91.5, 91.52, 172.3, 320.1, 252.3; 536/24.32, 24.33, 23.1; 935/77, 78

[56] References Cited

U.S. PATENT DOCUMENTS 4,870,006  9/1989  Dragon et al. ........................ 435/7

OTHER PUBLICATIONS

Lerner, R. A., (1984) Antibodies of Predetermined Specificity in Biology and Medicine, *Advances in Immunology* 36:1–43.
Pollard–Knight, Technique (1990) 2:113–132.
Brogan et al. Molec & Cellular Probes (1992) 6:411–416.
Roberts et al Israel J. Med Sci (1987) 23:618–620.

*Primary Examiner*—Stephanie W. Zitomer
*Assistant Examiner*—Carla Myers
*Attorney, Agent, or Firm*—Scully, Scott, Murphy & Presser

[57] ABSTRACT

The present invention is directed to a rapid and sensitive method for detecting *Mycoplasma hominis* using *M. hominis*-specific probes, oligonucleotides or antibodies. In particular a target sequence can be amplified by in vitro nucleic acid amplification techniques, detected by nucleic acid hybridization using the subject probes and oligonucleotides or detected by immunoassay using *M. hominis*-specific antibodies. *M. hominis*-specific nucleic acids which do not recognize or hybridize to genomic nucleic acid of other Mycoplasma species are also provided.

76 Claims, 8 Drawing Sheets

SEQ ID NO: 1
5' AAGCTTTAGT TAATTATGCA AAAGAGTATA CTGAATTTGA AGATATGGGG
51  ACTACAATGG TTGTTGCCCT CATTTTTAAT GCAAATGGTT TAGCTTATGT
101 CTTTAATATT GGTGATTCAC GCTTGTATGC ATACAATGGA TTACTTTATC
151 AAATCACAGA AGATCAAAAT TATTTATATC AGTTAATGAG AGAATTTAAT
201 TTAACATACG AAGAAGCAGC ATTAGATCCT AATTCATACA AACTTATAAG
251 TTGTCTAGGA CCAAATAAAA AAACCAATTG TCAATCATTT TTTATATCAC
301 AAAAATCAGC AGTTAAATAT TATTTATTAA CATCCGATGG ATTACACGAT
351 TATGTTTCTA AACCAATAAT AGAAACTGTT TTGCAAACAA ATAAGAGTTT
401 AAAAGATAAG TTAAACCTTC TAATAAAATA TGCCAAAAAA AATCTTTCAA
451 AAGACAATAT AACCGGAATT C

SEQ ID NO: 3
5' GGTGATTCAC GCTTGTATGC ATACAATGGA TTACTTTATC
41  AAATCACAGA AGATCAAAAT TATTTATATC AGTTAATGAG AGAATTTAAT
91  TTAACATACG AAGAAGCAGC ATTAGATCCT AATTCATACA AACTTATAAG
141 TTGTCTAGGA CC

SEQ ID NO:4:  5'-CTACAATGGT TGTTGCCCTC-3'
SEQ ID NO:5:  5'-GGTGATTCAC GCTTGTATGC-3'
SEQ ID NO:6:  5'-GGTCCTAGAC AACTTATAAG-3'
SEQ ID NO:7:  5'-ATCGTGTAAT CCATCGGATG-3'

FIG. 1a

SEQ ID NO:8

```
  5'ATCTGATGAA ACTAAATTTA TTGTTGTTAA AGTTTTAGAT ATTGGTGATG
 51   AAAAACAACA AATGGTTGTT TATGATGAAT TACGAATTTC AAATTTAATT
101   AAGAATTCAA ACTCTGATAA AAGAAGTTAT ATCATGGAAT ATTATGAATA
151   TTTCGAAAGT GGTTCATTAG AAACTGATGA TAAACGAATT TACATTGTTT
201   TTGAATATAT TGATGGTTTA ACATTGCGTG AATATCTTGA TGAATTTAAA
251   ACAGTTACTT ATGTTAAAGC TGTGAATATC GTCAGGTGCT-3'
```

SEQ ID NO:9:   5'-ACTAAATTTATTGTTGTTAA-3'
SEQ ID NO:10:  5'-CAATGTAAATTCGTTTATCA-3'
SEQ ID NO:11:  5'-TCGAACGAAGCCTTTTAGGC-3'
SEQ ID NO:12:  5'-CCAAAAGCGTCGCAAACGCG-3'
SEQ ID NO:13:  5'-TACAGTTTTTGATACAGCTA-3'
SEQ ID NO:14:  5'-CAGTGATAGTCCAAGTTGGC-3'
SEQ ID NO:15:  5'-TGTAGTGATCATATCAGAGTG-3'
SEQ ID NO:16:  5'-GACCTATTTTACTTGCGCTAT-3'

FIG. 1b 5,595,871

DETECTION AND PREVENTION OF MYCOPLASMA HOMINIS INFECTION

This invention was made with United States Government support by the Air Force Office of Scientific Research under a subcontract to University Energy Systems contract numbers F49620-85-C001 and F49620-88-C0053 awarded by the Air Force Office of Scientific Research. The United States Government may have some rights in the present invention.

FIELD OF THE INVENTION

The present invention is directed to rapid and sensitive methods for detecting Mycoplasma hominis using *M. hominis*-specific probes, oligonucleotides, polypeptides and antibodies. In particular a target sequence can be amplified by in vitro nucleic acid amplification techniques or directly detected by immunoassay or nucleic acid hybridization. *M. hominis*-specific nucleic acids and antibodies are provided which can be used in these techniques. The present invention further provides isolated *M. hominis*-specific polypeptides as antigens or vaccines against *M. hominis*.

BACKGROUND OF THE INVENTION

*M. hominis* and a related mycoplasma species, *Ureaplasma urealyticum*, cause about half of all non-gonococcal venereal diseases. In addition, about 70% of patients with a gonococcal infection are concurrently infected with a mycoplasma.

*M. hominis* is associated with pathological conditions in the urogenital tract of men and the upper urogenital tract of women. For example, *M. hominis* has been implicated as a cause of nongonococcal urethritis, urethroprostatitis, vaginitis, endometritis, pelvic inflammatory disease, cervicitis, infertility, postpartum septicemia, pregnancy wastage, low birth weights and birth defects.

*M. hominis* is often transmitted by sexual contact and can be transmitted to neonates born of infected mothers, resulting in infection of fetuses and infants. *M. hominis* can cause chorioamnionitis, spontaneous abortion of preterm fetuses, skin abscesses, central nervous system infections and fatal fetal pneumonia. (See reviews by Cassell et al. (1991) *Clin. Perinatol.* 18:241–262; Cassell et al. (1984) *Adv. Exp. Med. Biol.* 224:93–115; and Cassell et al. (1983) *Sex. Transm. Dis.* 10:294–302.)

*M. hominis* lack a cell wall and are among the smallest of free living organisms, having a size of only about 0.2 to 0.3 μm. The genome of *M. hominis* is unusual in its small size ($5 \times 10^8$ daltons) and low guanine/cytosine content. *M. hominis* are difficult to culture because of their fastidious nutritional requirements and slow growth rates. Such properties make diagnosis of *M. hominis* infection by the current bacteriological culturing procedures difficult and time consuming. For example, diagnosis of *M. hominis* infection by such procedures can require up to 2 to 6 days for positive identification depending on the amount of the initial inoculum. Since diagnosis of *M. hominis* infection by bacteriological culturing procedures is time consuming, expensive and requires a high degree of expertise, few clinical laboratories include *M. hominis* in the list of organisms for which they provide detection services. These disadvantages often discourage physicians from requesting diagnostic tests for *M. hominis* and result in a considerable loss of time in treatment of patients. Consequently, the etiologic role of *M. hominis* in various diseases and the complete range of tissue tropism for this pathogen has not been elucidated.

*M. hominis*-specific nucleic acid probes and antibodies offer an approach to surmount the difficulties inherent in identification and detection of *M. hominis* by traditional bacteriological culture procedures. Rapid and effective immunoassays for *M. hominis* can dramatically decrease the time and expense of diagnosing *M. hominis* infection. Specific nucleic acid probes for *M. hominis* are useful in conventional hybridization detection procedures, as well as in other procedures, such as in situ hybridization, solution hybridization and in vitro nucleic acid amplification with subsequent detection. The latter method for *M. hominis* detection provides a practical means to enhance detection sensitivity relative to conventional hybridization technology. Moreover, polypeptides which are uniquely encoded within the *M. hominis* genome have utility as antigens or vaccines against *M. hominis*.

Although the sequence of the *M. hominis* 16S ribosomal RNA is known (Weisberg et al. (1989) *J. Bacteriol.* 171:6455–6467), there has been no publication of a nucleotide or polypeptide sequence which is specific for *M. hominis*.

SUMMARY OF THE INVENTION

The present invention provides rapid and sensitive methods for detection of *M. hominis* in animals, especially in human and veterinary clinical samples. In particular, the present invention provides nucleic acid probes, oligonucleotides and antibodies which are specific for *M. hominis*, i.e. selective for *M. hominis* and not other Mycoplasma species. The subject probes, oligonucleotides and antibodies can be used in detection assays to establish whether *M. hominis* microorganisms are present in a sample.

In one embodiment, a method of detecting *M. hominis* uses in vitro nucleic acid amplification. This method includes contacting a sample to be tested for the presence of an *M. hominis* target nucleic acid with an amplification enzyme and at least one *M. hominis*-specific oligonucleotide for a time and under conditions sufficient to produce copies of the target nucleic acid. Such copies are then detected by conventional means. According to the present invention any *M. hominis*-specific oligonucleotide can be used which does not detectably hybridize to genomic DNA of other Mycoplasma including *U. urealyticum, M. genitalium, M. hyorhinis, M. orale, M. pneumoniae* or *M. salivarium*. However in one embodiment the oligonucleotide includes a nucleotide sequence of at least about 14 contiguous nucleotides which hybridizes to either the *M. hominis* DNA in plasmid pMhom120 or to SEQ ID NO:1. Preferred means of in vitro nucleic acid amplification include polymerase chain reaction (PCR), transcription-based amplification systems (TAS), self-sustained sequence replication (3SR) systems, ligase-based amplification systems (LAS), Qβ replicase RNA replication systems and run-off transcription.

In another embodiment, the present invention provides a method of detecting *M. hominis* by nucleic acid hybridization. This method includes contacting a sample to be tested for the presence of an *M. hominis* target nucleic acid with at least one nucleic acid probe for a time and under conditions sufficient to permit hybridization between the nucleic acid probe and the *M. hominis* target nucleic acid. Such hybridization is then detected or measured by conventional means. Again any *M. hominis*-specific probe can be used which does not detectably hybridize to genomic DNA of other Mycoplasma, including *U. urealyticum, M. genitalium, M. hyorhinis, M. orale, M. pneumoniae* or *M. salivarium*. However, in one embodiment the probe includes a nucleotide sequence of at least about 14 contiguous nucleotides which hybridizes to the *M. hominis* DNA in plasmid pMhom120 or to SEQ ID NO:1. Preferred forms of nucleic acid hybridization include solid-phase-based hybridization, i.e. hybridization on filters or beads, solution phase hybridization, and in situ hybridization.

A further embodiment of the present invention provides a method for detecting *M. hominis* by contacting a sample to be tested for the presence of *M. hominis* with an antibody reactive with one of the present *M. hominis*-specific polypeptides for a time and under conditions sufficient to form a polypeptide-antibody complex, and detecting the complex.

The present invention also provides isolated nucleic acids which have a nucleotide sequence of at least about 14 nucleotides and which are selected from genomic *M. hominis* DNA such that the nucleic acid can hybridize to the *M. hominis* DNA and do not hybridize to genomic DNA of *U. urealyticum, M. genitalium, M. hyorhinis, M. orale, M. pneumoniae* or *M. salivarium*. Such an isolated nucleic acid preferably does not encode 16S ribosomal RNA. In a preferred embodiment such isolated nucleic acids are at least about 70% homologous to SEQ ID NO:1. Examples of the present isolated nucleic acids include those having SEQ ID NO:1 and 3–7.

The present invention is also directed to expression vectors which include any of the present *M. hominis*-specific nucleic acids, e.g. an isolated nucleic acid including the *M. hominis* DNA in pMhom120 or SEQ ID NO:1 or SEQ ID NO:3. In such expression vectors the present nucleic acids are operably linked to segment of the vector which can effect expression of the nucleic acid, e.g. a promoter, a translational start signal and the like.

The present invention is further directed to a host cell containing any of the present nucleic acids or expression vectors.

The present invention also provides an isolated *M. hominis* polypeptide encoded by any one of the present isolated nucleic acids and antibodies reactive therewith. In a related embodiment, the present invention provides an isolated *M. hominis* peptide including at least about 6 contiguous amino acids of SEQ ID NO:2 and antibodies reactive therewith. Such a peptide is preferably antigenic or immunologically specific for *M. hominis*.

In another embodiment, the present invention provides a process for producing polypeptides encoded by the instant nucleic acids, e.g. a polypeptide having a sequence comprising SEQ ID NO:2, which includes culturing one of the instant host cells for a time and under conditions sufficient to produce the polypeptide.

The present invention is also directed to a composition which includes one of the present polypeptides or peptides and a pharmaceutically acceptable carrier.

A further aspect of this invention provides kits which include one or more of the present nucleic acids, oligonucleotides, polypeptides or antibodies. Such kits can be used in the practice of the methods described herein.

BRIEF DESCRIPTIONS OF THE DRAWINGS

FIG. 1a depicts the sequence of isolated *M. hominis* nucleic acids having SEQ ID NO:1 and SEQ ID NO:3, as well as preferred oligonucleotides having sequences of SEQ ID NO:4, SEQ ID NO:5, SEQ ID NO:6 and SEQ ID NO:7, capable of selective hybridization with *M. hominis* nucleic acids. The positions of SEQ ID NO:4–7 are indicated with underlining in SEQ ID NO:1. The positions of SEQ ID NO:5 and SEQ ID NO:6 are indicated with underlining in SEQ ID NO:3. The position of SEQ ID NO:3 within SEQ ID NO:1 is provided in bold.

FIG. 1b depicts the sequence of some isolated *U. urealyticum*-specific nucleic acids having SEQ ID NO: 8–16 which can be used in conjunction with the present methods, nucleic acids and oligonucleotides to simultaneously or separately detect *U. urealyticum* and *M. hominis*.

FIG. 2a shows EcoRI-digested genomic DNA from several Mycoplasma species and from *M. hominis* after separation in an 1% agarose gel. Lane 1 contains a 1 Kb ladder of DNA size markers. Lanes 2–8 contain genomic DNA from the following species: (2) *Mycoplasma genitalium*, (3) *Mycoplasma hominis*, (4) *Mycoplasma hyorhinis*, (5) *Mycoplasma orale*, (6) *Mycoplasma pneumoniae*, (7) *Mycoplasma salivarium* and (8) *Ureaplasma uealyticum*.

FIG. 2b shows an autoradiogram of a Southern blot of the gel depicted in FIG. 2a which was probed with the *M. hominis* DNA inserted into pMhom120. Lane 1 contains a 1 Kb ladder of DNA size markers. Lanes 2–8 contain genomic DNA from the following species: (2) *Mycoplasma genitalium*, (3) *Mycoplasma hominis*, (4) *Mycoplasma hyorhinis*, (5) *Mycoplasma orale*, (6) *Mycoplasma pneumoniae*, (7) *Mycoplasma salivarium* and (8) *Ureaplasma uealyticum*. As illustrated, the pMhom120 insert hybridized only with *M. hominis* genomic DNA.

FIG. 3 depicts an autoradiogram of a dot blot hybridized with a probe made from the *M. hominis* DNA inserted in plasmid pMh5 (i.e. SEQ ID NO:1). Spots 1–7 contain genomic DNA from the following species: (1) *Mycoplasma genitalium*, (2) *Mycoplasma hominis*, (3) *Mycoplasma hyorhinis*, (4) *Mycoplasma orale*, (5) *Mycoplasma pneumoniae*, (6) *Mycoplasma salivarium* and (7) *Ureaplasma uealyticum*. As illustrated this probe hybridized only with *M. hominis* genomic DNA.

FIG. 4a depicts an agarose gel containing electrophoretically separated PCR products from template genomic DNAs obtained from (2) *M. genitalium*, (3) *M. hominis*, (4) *M. hyorhinis*, (5) *M. orale*, (6) *M. pneumoniae*, (7) *M. salivarium*, (8) *U. urealyticum*, (9–17) clinical samples as test samples for *M. hominis*, (18) *M. hominis* and (19) negative control. Lane (1) contains a 1 Kb ladder of DNA size markers.

FIG. 4b depicts a Southern blot of the gel depicted in FIG. 4b which was hybridized with a probe made from the *M. hominis* DNA inserted in plasmid pMh5 (i.e. SEQ ID NO:1). The separate lanes contain the PCR product from template genomic DNAs obtained from (2) *M. genitalium*, (3) *M. hominis*, (4) *M. hyorhinis*, (5) *M. orale*, (6) *M. pneumoniae*, (7) *M. salivarium*, (8) *U. urealyticum*, (9–17) clinical samples as test samples for *M. hominis*, (18) *M. hominis* and (19) negative control. Lane (1) contains a 1 Kb ladder of DNA size markers. As illustrated this probe detected *M. hominis* DNA in lanes 3, 10, 12, 13, 15, 16 and 18.

FIG. 5 depicts an ethidium bromide stained agarose gel containing the PCR amplified products generated from different amounts of *M. hominis* genomic DNA. Lane 1 contains a 100 bp ladder of molecular weight markers. Lanes 2–7 contain the PCR product obtained from decreasing amounts of genomic *M. hominis* template DNA, i.e. lane 2=100 femtograms (fg); lane 3 =10 fg; lane 4=1 fg; lane 5=100 attograms (ag); lane 6=10 ag; and lane 7=1 ag. Lane 8 is a negative control containing water in place of DNA. FIG. 5 illustrates that the present in vitro nucleic acid amplification methods are highly sensitive, having the capability of detecting as little as 10 fg ($10 \times 10^{-15}$ g) of *M. hominis* genomic DNA.

DETAILED DESCRIPTION OF THE INVENTION

Figure 2A:
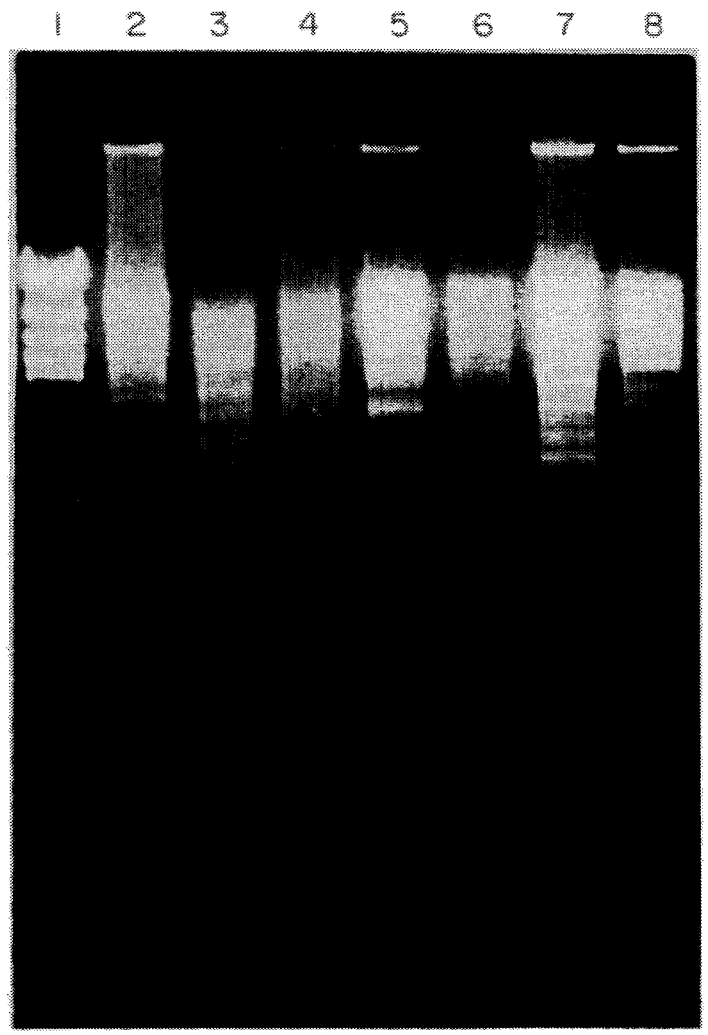

The present invention relates to detection of a small microorganism, *M. hominis,* and prevention of the variety of human disease conditions associated with *M. hominis* infection, including nongonococcal urethritis, urethroprostatitis, vaginitis, endometritis, pelvic inflammatory disease, cervicitis, infertility, postpartum septicemia, pregnancy wastage, low birth weights, birth defects, chorioamnionitis, spontaneous abortion of preterm fetuses, skin abscesses, central nervous system infections and fatal fetal pneumonia.

In one embodiment, the present invention provides isolated nucleic acids which can specifically detect *M. hominis.* Surprisingly, such nucleic acids can hybridize with *M. hominis* nucleic acids without hybridizing to nucleic acids, e.g. genomic DNA, rRNA and mRNA, from closely related Mycoplasma species such as *Ureaplasm urealyticum, Mycoplasma genitalium, Mycoplasma hyorhinis, Mycoplasma orale, Mycoplasma pneumoniae* and *Mycoplasma salivarium.*

According to the present invention, the subject isolated nucleic acids are isolated from a genomic library of *M. hominis* DNA by screening with a labeled probe made from *M. hominis* genomic DNA and then screening again with a labeled probe made from Ureaplasm or non-*M. hominis* Mycoplasm genomic DNA. In this manner, *M. hominis*-specific nucleic acids have been and can be identified as nucleic acids that hybridize only with *M. hominis* genomic DNA.

Construction of genomic libraries, screening procedures and general recombinant DNA techniques are available to the skilled artisan in any of many texts or manuals available for such procedures. One such manual is provided by Sambrook, et al. (1989) *Molecular Cloning: A Laboratory Manual,* Vols. 1–3, Cold Spring Harbor Press, Cold Spring Harbor, N.Y. Accordingly the skilled artisan can use available hybridization procedures and the present teaching on how to identify *M. hominis*-specific nucleic acids using *M. hominis* and related Mycoplasma genomic probes to obtain the subject nucleic acids.

Preferred isolated nucleic acids of the present invention include the *M. hominis* DNA inserts in plasmids pMhom120, pMh5 and *M. hominis*-specific DNA fragments of such inserts. As provided herein, such *M. hominis*-specific DNA fragments can selectively hybridize to an *M. hominis* nucleic acid.

pMhom120 consists of an approximate 2000 base pair (bp) EcoRI fragment inserted into pUCl18. When digested with HindIII, pMhom120 yielded two HindIII inserts having approximate sizes of 500 and 1500 bp. The smaller HindIII restriction fragment of about 500 bp was subcloned into pUCl18 to produce pMh5. The pMh5 insert has been sequenced and found to be 471 bp in size; this sequence is identified herein as SEQ ID NO:1. Plasmic pMhom120 was deposited with the American Type Culture Collection, 12301 Parklawn Drive, Rockville, Md. on Apr. 19, 1996 and was assigned Accession Number 97512.

SEQ ID NO:1 encodes a polypeptide whose amino acid sequence is identified herein as SEQ ID NO:2. Since SEQ ID NO:1 is *M. hominis*-specific and forms the template for the polypeptide encoded therein, the SEQ ID NO:2 polypeptide is also *M. hominis*-specific.

In another embodiment, the isolated nucleic acids of the present invention include regions or segments of the *M. hominis* genome which do not encode an open reading frame or polypeptide. In general such non-coding regions may be more highly diverged between related species than are coding regions, since conservation of the function provided by a coding region is often needed for survival. Therefore, non-coding regions can be more species-specific than coding regions in the genomes of closely related species.

The present invention includes nucleic acid probes and oligonucleotides derived from the subject *M. hominis*-specific nucleic acids. Any of these nucleic acids, probes or oligonucleotides have a nucleotide sequence which is sufficiently complementary to hybridize to a nucleotide sequence derived from genomic *M. hominis* DNA.

Complementarity between nucleic acids is the degree to which the bases in one nucleic acid strand can hydrogen bond, or base pair, with the bases in a second nucleic acid strand. As used herein, sufficient complementary means that a sufficient number of the nucleotides in the subject isolated *M. hominis* nucleic acids and oligonucleotides form base pairs with nucleotides in an *M. hominis* nucleic acid target to generate a stable hybridization complex at about room temperature (i.e. at about 20° C. to about 25° C.).

In addition, the sufficient number of base pairs required by the present invention is that number of base pairs which provides selective hybridization to an *M. hominis* nucleic acid target. As used herein selective hybridization means that hybridization to an *M. hominis* nucleic acid target is detectably greater than is hybridization to nucleic acids from Ureaplasm or non-*M. hominis* Mycoplasm genomic DNA. For example, substantially more hybridization occurs to Southern blot of *M. hominis* DNA, than to a Southern blot of DNA from any of the above-listed closely related Mycoplasma.

According to the present invention, selective hybridization is achieved when the hybridization to the *M. hominis* nucleic acid target is at least about two- to about five-fold greater than is the hybridization to a nucleic acid target from another Mycoplasma species. Preferably there is at least a ten-fold difference in the amount of hybridization to the *M. hominis* nucleic acid target and the amount of hybridization to a nucleic acid target from another Mycoplasma species.

Complementarity can sometimes be conveniently described by the percentage, i.e. proportion, of nucleotides which can form base pairs between two nucleic acid strands or within a specific region or domain of the two strands. When expressed or measured by percentage of base pairs formed, the degree of complementarity can range from at least about 70% to full, i.e. 100% complementarity. In general, the overall degree of complementarity between an *M. hominis* nucleic acid and the present oligonucleotides or nucleic acids is at least about 80%, and preferably about 90% or higher.

Therefore, according to the present invention the degree of complementarity that the present oligonucleotides and isolated nucleic acids have with the *M. hominis* target nucleic acid need not be 100% so long as selective hybridization to *M. hominis* can be achieved and detected.

The term homology, as used herein, is the degree of sequence identity between two nucleic acid strands. When a target is a double-stranded nucleic acid, one target strand is complementary, and the other target strand is homologous, to a probe or oligonucleotide of the present invention. Moreover the sequence listing provided herein recites the sequence of only one strand. However as provided herein some of the sequences described in the sequence listing are intended to be double-stranded. Accordingly, when a double-stranded target is identified by SEQ ID NO, a probe or oligonucleotide can also be homologous to the recited sequence and hence can hybridize to the strand not recited in the sequence listing.

The degree of homology can also be described by the percentage of identical nucleotides in two nucleic acid sequences. In particular, the degree of homology between a target nucleic acid and a probe or oligonucleotide of the present invention can vary so long as selective hybridization is attained, and can range from at least about 70% to about 100% homology. In general, the overall degree of homology between an *M.. hominis* nucleic acid and the present oligonucleotides or nucleic acids is at least about 80%, and preferably about 90% or higher.

In a preferred embodiment, the present invention provides isolated nucleic acids each having a nucleotide sequence of at least about 14 contiguous nucleotides which is at least about 70% complementary to either strand of the *M. hominis* DNA insert in plasmid pMhom120. In a more preferred embodiment such isolated nucleic acids are at least about 70% complementary to either strand of SEQ ID NO:1.

The length of the nucleic acids or oligonucleotides for use in detecting *M. hominis* depends on several factors including the nucleotide sequence and the temperature at which these nucleic acids are hybridized or used during in vitro nucleic acid amplification. The considerations necessary to determine a preferred length for a nucleic acid or oligonucleotide are well known to the skilled artisan.

For example, as is known to the skilled artisan, the length of a short nucleic acid or oligonucleotide can relate to its hybridization specificity or selectivity. When a test sample contains complex mixtures of nucleic acids, e.g. mammalian genomic DNA, oligonucleotides which are shorter than about 14 nucleotides may hybridize to more than one site in the mammalian genome, and accordingly would not have sufficient hybridization selectivity for detecting a single target nucleic acid. However the sequence of a nucleic acid which is about 14–15 nucleotides is generally represented only once in a mammalian genome (Sambrook et al. 1989 *Molecular Cloning: A Laboratory Manual*, Vol. 2, Cold Spring Harbor Press, Cold Spring Harbor, N.Y.; pp. 11.7–11.8). Accordingly, to eliminate cross hybridization with mammalian genomic DNA, the nucleic acids and oligonucleotides of the present invention are generally at least about 14 nucleotides long.

However, as is known to the skilled artisan nucleic acids or oligonucleotides which are shorter than 14 nucleotides, e.g. oligonucleotides of about 10 to about 12 or more nucleotides, can be specific for a given target. Therefore the term at least "about" is used to include any such nucleic acids and oligonucleotides which are less than 14 nucleotides long but which selectively hybridize to an *M. hominis* target nucleic acid.

Preferably, the present nucleic acids and oligonucleotides are at least 16 nucleotides in length. More preferred nucleic acids and oligonucleotides are at least 17 nucleotides in length (Sambrook et al., pp. 11.7–11.8).

Nucleic acid probes of the present invention contain at least about 14 nucleotides to about 3000 nucleotides. Oligonucleotides of the present invention typically contain at least about 14 to about 150 or more nucleotides.

Preferred nucleic acid probes and oligonucleotides include the *M. hominis* DNA in pMhom120 and pMh5 as well as nucleic acids having SEQ ID NOS:1 and 3–7.

In another embodiment, the present invention is directed to an RNA transcribed from the present isolated nucleic acids (i.e. DNAs). For example, such an RNA can be transcribed from an isolated nucleic acid having SEQ ID NO:1 or SEQ ID NO:3, or from the *M. hominis* DNA in pMhom120. Methods for producing and purifying such RNAs, e.g. from an expression vector containing one of the present nucleic acids either in vivo or in vitro, are well known to the skilled artisan (e.g. see Sambrook et al. vols. 1–3). Such methods are also described in more detail hereinbelow.

A further embodiment of the present invention includes an isolated nucleic acid having an antisense nucleotide sequence of an RNA transcribed by any of the present nucleic acids. Such an antisense nucleic acid can include a nucleotide sequence of at least about 14 contiguous nucleotides which is at least about 70% complementary to an RNA transcribed by any of the present nucleic acids.

Stated in another way, an antisense nucleic acid of the present invention can include a nucleotide sequence of at least about 14 contiguous nucleotides which is at least about 70% homologous to a template strand of one of the present isolated DNAs. As used herein the template strand is the DNA strand read by RNA polymerase; such a template strand is complementary to an RNA synthesized therefrom.

For example the present antisense nucleic acids can be at least about 70% homologous to the template strand of the *M. hominis* DNA insert in plasmid pMhom120, of SEQ ID NO:1 or of SEQ ID NO: 3.

The nucleic acids, probes and oligonucleotides of the present invention can be prepared by conventional methods, for example, by recombinant techniques or by synthetic techniques. Recombinant techniques include isolation of restriction fragments, insertion of such restriction fragments into vectors, nick translation of an isolated nucleic acid, expression of an RNA from an expression vector containing an isolated nucleic acid of the present invention, and other known techniques, for example, as provided, for example, by Sambrook et al.

An antisense nucleic acid is an isolated DNA or RNA which is complementary to a transcribed sense RNA. Such an antisense nucleic acid can be an oligonucleotide or a longer nucleic acid. Longer antisense DNA can be made enzymatically or isolated, e.g. by strand separating gel electrophoresis or density gradient centrifugation. An antisense RNA can be synthesized from an antisense gene made by juxtapositioning to a promoter, in reverse orientation, an isolated DNA having a sequence for the sense RNA. RNA transcribed from such an antisense gene is antisense RNA.

Short sense or antisense oligonucleotides and nucleic acids, e.g. of up to about 50 nucleotides, can be chemically synthesized by available synthetic procedures for nucleic acids. Chemical synthesis of nucleic acids is well known in the art and can be achieved by solution or solid phase techniques. Moreover, oligonucleotides or nucleic acids of defined sequence can be purchased commercially or can be made by any of several different synthetic procedures including the phosphoramidite, phosphite triester, H-phosphonate and phosphotriester methods, typically by automated synthesis methods. Modified bases can also be incorporated into the nucleic acid. If modified phosphodiester linkages are used the synthetic procedures are altered as needed according to known procedures. In this regard, Uhlmann et al. (1990 Chemical Reviews 90:543–584) provide references and outline procedures for making nucleic acids with modified bases and modified phosphodiester linkages.

Enzymatic methods are also available for DNA, RNA or oligonucleotide synthesis. For DNA and oligodeoxyribonucleotide synthesis, these methods frequently employ Klenow, T7, T4, Taq or *E. coli* DNA polymerases, e.g. as described in Sambrook et al. Enzymatic methods of RNA or oligoribonucleotide synthesis frequently employ SP6, T3 or T7 RNA polymerase as described, for example, in Sambrook et al. Reverse transcriptase can also be used to synthesize DNA from RNA.

To prepare an a nucleic acid or oligonucleotide enzymatically requires a template nucleic acid which can either be synthesized chemically, or be obtained as mRNA, genomic DNA, cloned genomic DNA, cloned cDNA or recombinant DNA. Some enzymatic methods of DNA or oligodeoxyribonucleotide synthesis can require a short primer oligonucleotide; this primer can be obtained or synthesized by any available procedure.

After enzymatic or chemical synthesis, nucleic acids and oligonucleotides can be purified by polyacrylamide gel electrophoresis, or by any of a number of chromatographic methods, including gel, ion-exchange and high pressure liquid chromatography. To confirm a nucleotide sequence, nucleic acids and oligonucleotides can be subjected to DNA sequencing by available procedures, including Maxam and Gilbert sequencing, Sanger sequencing, capillary electrophoreses sequencing the wandering spot sequencing procedure or by using selective chemical degradation of oligonucleotides bound to Hybond paper. Sequences of short oligonucleotides can also be analyzed by plasma desorption mass spectroscopy or by fast atom bombardment (McNeal et al. (1982) *J. Am. Chem. Soc.* 104:976; Viari et al. (1987) *Biomed. Environ. Mass Spectrom.* 14:83; Grotjahn et al. (1982) *Nucleic. Acid Res.* 10:4671). Sequencing methods are also available for RNA oligonucleotides.

Another aspect of this invention provides a method of detecting Mycoplasma hominis which includes contacting a sample to be tested for the presence of an *M. hominis* target nucleic acid with an amplification enzyme and at least one *M. hominis*-specific oligonucleotide for a time and under conditions sufficient to produce copies of the target nucleic acid and detecting the copies. In one embodiment, the oligonucleotide can include a nucleotide sequence of at least about 14 contiguous nucleotides which hybridizes to the *M. hominis* nucleic acids in pMhom120. Preferably the oligonucleotide includes a nucleotide sequence of at least about 14 contiguous nucleotides which hybridizes to SEQ ID NO:1.

Moreover an oligonucleotide utilized for in vitro amplification of an *M. hominis* target nucleic acid does not substantially or detectably produce copies of a nucleic acid target from any of *U. urealyticum, M. genitalium, M. hyorhinis, M. orale, M. pneumoniae* or *M. salivarium*.

As provided herein, the *M. hominis* target nucleic acid for in vitro amplification is that segment of nucleic acid which is copied during amplification. Accordingly the oligonucleotide(s) employed for amplification hybridize to only a portion of the target nucleic acid. This portion is referred to herein as the oligonucleotide binding site. An oligonucleotide binding site can define the 3' or 5' end of the *M. hominis* target nucleic acid. Therefore when copies of the target nucleic acid are made during amplification the actual 3' or 5' ends of such copies can be composed of oligonucleotides which, e.g. act as primers for synthesis of the copy. Alternatively a portion or the whole of an oligonucleotide sequence can be copied during the amplification procedure or the oligonucleotide sequence may not be copied at all but instead forms a recognition site for initiation of nucleic acid synthesis by an amplification enzyme.

As used herein, the method of amplifying *M. hominis* target sequences are methods of in vitro nucleic acid amplification which include any procedure using an oligonucleotide to direct synthesis of a nucleic acid copy of the target sequence. In vitro nucleic acid amplification thus allows selective synthesis of a specific DNA or RNA target relative to the complex bulk of nucleic acid present in a sample. The specificity of the process is determined by the oligonucleotides, e.g. oligonucleotide primers, capable of hybridizing with the *M. hominis* nucleic acid to the exclusion of nucleic acids from Ureaplasm and non-*M. hominis* Mycoplasma species.

Conditions for in vitro nucleic acid amplification generally include temperature and salt concentrations permitting selective hybridization between the oligonucleotide and target, e.g. stringent hybridization conditions. Preferably such conditions permit little or no detectable hybridization to nucleic acids from non-*M. hominis* Mycoplasma species or to non-target sites in *M. hominis* nucleic acids. A preferred hybridization temperature is about 5° C. to about 10° C. below the melting temperature of the target: oligonucleotide hybrid (Sambrook et al.). However, this hybridization temperature can readily be varied to accommodate other considerations such as the thermal unstability of the amplification enzyme.

Conditions for in vitro nucleic acid amplification also include those salt, cation, pH and temperature conditions required for enzymatic activity of the amplification enzyme. For example, some amplification enzymes require a cation such as magnesium for optimal activity. Moreover some amplification enzymes like the *Thermus aquaticus* or*Thermococcus litoralis* DNA polymerases are stable for extended periods of time at 98° C., others such as the SP6 or T7 RNA polymerases are rapidly denatured at a temperature of about 65° C. Optimal salt, cation, pH and temperature conditions for obtaining amplification enzyme activity are readily available to the skilled artisan, e.g. from a commercial manufacturer of these enzymes.

Moreover to permit copies of an *M. hominis* target nucleic acid to be made the appropriate nucleotide subunits are also provided to the reaction mixture including the target nucleic acid, e.g. ATP, CTP, GTP, UTP, dATP, dCTP, dGTP or dTTP.

In general DNA polymerases can only copy DNA from a single-stranded target. Therefore the present methods can include at least one denaturing step for double-stranded target nucleic acids. Such methods can further include at least one denaturing step for separating a DNA or RNA copy from a target nucleic acid.

In vitro nucleic acid amplification techniques are known in the art. A review of such techniques can be found in Kwoh et al. (1990) *Am. Biotechnol. Lab.* 8:14. In vitro nucleic acid amplification techniques include polymerase chain reaction (PCR), transcription-based amplification system (TAS), self-sustained sequence replication system (3SR), ligation amplification reaction (LAR), ligase-based amplification system (LAS), Qβ RNA replication system and run-off transcription.

PCR is a method for primer-directed enzymatic amplification of target nucleic acids. PCR synthesis occurs by repeated cycles of heat denaturation of the target, primer annealing and primer extension. These cycles can be performed manually or, preferably, automatically. Thermal cyclers such as the Perkin-Elmer Cetus cycler are specifically designed for automating the PCR process, and are preferred. The number of cycles per round of synthesis can be varied from 2 to more than 50, and is readily determined by considering the source and amount of the nucleic acid template, the desired yield and the procedure for detection of the synthesized DNA fragment. PCR techniques and many variations of PCR are known. Basic PCR techniques are described by Saiki et al. (1988 Science 239:487–491) and by U.S. Pat. Nos. 4,683,195, 4,683,202 and 4,800,159, which are incorporated herein by reference.

The conditions generally required for PCR include temperature, salt, cation, pH and related conditions needed for efficient copying of the target. PCR conditions include repeated cycles of heat denaturation (i.e. heating to at least about 95° C.) and incubation at a temperature permitting target: oligonucleotide hybridization and copying of the target by the amplification enzyme. Heat stable amplification enzymes like the *Thermus aquaticus* or *Thermococcus litoralis* DNA polymerases are commercially available which eliminate the need to add enzyme after each denaturation cycle. The salt, cation, pH and related factors needed for amplification enzyme activity are available from commercial manufacturers of amplification enzymes.

The transcription-based amplification system (TAS) utilizes a sample (sense) RNA template from which a double stranded complementary DNA (i.e. cDNA) is made. One or more of the oligonucleotides used for synthesis of the cDNA contains an RNA polymerase recognition site. An RNA polymerase capable of recognizing and synthesizing RNA starting at that recognition site is then added to produce many RNA copies of the cDNA. To achieve even greater amounts of an RNA synthetic product, additional rounds of cDNA synthesis can be performed using the synthesized RNA as template and this additional cDNA can be used to make even more RNA product. RNA polymerases which can be used for TAS include, for example, SP6, T3, T7 and other RNA polymerases. TAS techniques are described by Kwoh et al.

Conditions for TAS amplification are generally determined by the temperature, salt, cation and pH requirements of the RNA polymerase employed. These conditions are readily available to the skilled artisan, e.g. as provided by commercial manufacturers of such RNA polymerases.

When a TAS technique is performed the subject oligonucleotides can contain an additional sequence which encodes a recognition or binding site for an RNA polymerase, e.g. a T7, T3 or SP6 RNA polymerase recognition sequence. RNA polymerase recognition sequences are well known in the art and are readily incorporated into the present oligonucleotides by the skilled artisan.

The self-sustained sequence replication (3SR) procedure involves continuous cycling of reverse transcriptase and RNA polymerase synthesis. 3SR utilizes RNase H enzymatic degradation of the RNA in an RNA:cDNA duplex, an innovation which eliminates thermal denaturation and repetitive addition of reagents. The 3SR procedure involves synthesis of a double stranded cDNA wherein the oligonucleotide used for synthesis of either the first or second cDNA strand, has an RNA polymerase recognition site. The double-stranded cDNA then acts as target for synthesis of either an antisense or sense RNA, depending on whether the first or second cDNA strand, respectively, has the RNA polymerase recognition site. Since there is no thermal denaturation step, the enzymes used for cDNA synthesis remain active and can produce more cDNA from the sense or antisense RNA product which can itself serve as a target for more RNA product. 3SR techniques are described by Kwoh et al.

Conditions for 3SR amplification are generally determined by the temperature, salt, cation and pH requirements of the reverse transcriptase and the RNA polymerase employed. These conditions are readily available to the skilled artisan, e.g. as provided by commercial manufacturers of such enzymes.

The 3SR procedure has some advantages over PCR or TAS in that all reagents are placed in a single tube and incubation is at a single temperature. Accordingly, no thermal cycling or repeated addition of reagents is required. 3SR is also more rapid than many other in vitro nucleic acid amplification procedures since an approximate $10^6$-fold amplification of a desired DNA or RNA can be achieved in about an hour.

DNA ligase can be used to synthesize DNA by repeatedly joining oligonucleotides hybridized to a template nucleic acid. Such procedures have been termed ligation amplification (LAR) and ligase-based amplification systems (LAS). LAR or LAS utilizes four oligonucleotides wherein two oligonucleotides hybridize to one strand of the target DNA and the other two hybridize to the complementary sequences. The adjacently hybridizing oligonucleotides are then joined by DNA ligase. After thermal denaturation, an additional cycle of hybridization and ligation can be performed. Each round of denaturation, hybridization and ligation increases the ligated product by about two-fold. Blunt end ligation of oligonucleotides hybridizing to complementary oligonucleotides can be controlled by adjusting the temperature of the ligation step.

Conditions for LAS include temperature, salt, cation, pH and the like needed for repeated rounds of denaturation, hybridization and ligation. Denaturation is generally performed at about 95° C. to about 100° C. Hybridization is perferably performed at about about 5° C. to about 10° C. below the melting temperature of the target:oligonucleotide hybrid, however slow cooling from the denaturation temperature can also lead to selective hybridization between the target and the oligonucleotide(s). The conditions needed for efficient ligation are well known to the skilled artisan (e.g. see Sambrook et al.). The LAS technique is also described by Kwoh et al.

An RNA can be synthesized from a nucleic acid by employing a Qβ replicase RNA replication system in which a first strand of a cDNA is made having a Qβ replicase 5'-recognition site lying on the 3'-side of an RNA polymerase recognition site. This is done with an oligonucleotide capable of hybridizing to an RNA target which also encodes the 5'-Qβ and RNA polymerase recognition sites in the correct positions. A second cDNA strand is then synthesized using an oligonucleotide encoding a Qβ 3'-recognition site. An RNA polymerase can then use the double-stranded cDNA as a template for synthesis of antisense RNA having, as 5' and 3' ends, the respective 5'- and 3'-Qβ replicase recognition sites. This antisense RNA can then serve as a template for Qβ replicase synthesis of sense and antisense RNA. This Qβ replicase technique is described by Kwoh et al.

In this regard, the subject oligonucleotides can contain additional nucleotide sequences which encode an RNA polymerase recognition site, the 5' Qβ replicase recognition site and the 3' Qβ replicase recognition site as necessary to conduct Qβ replicase RNA replication system. Such sites are well known in the art and can readily be incorporated in the oligonucleotides of the present invention.

A suitable amount of each oligonucleotide for in vitro nucleic acid amplification to enable detection of *M. hominis* is about 0.1 μmole to about 500 μmole, and preferably about 1 μmole to about 300 μmole. An especially preferred amount of each oligonucleotide is about 1 μmole to about 100 μmole. Other reagents as needed are added to the amplification reaction mixtures. Such reagents include nucleotides, additional enzymes, a source of a high-energy phosphate (e.g. ATP), and the like. Moreover the target nucleic acid can be either DNA, RNA or both and depends on the in vitro nucleic acid amplification system selected. In many of these procedures DNA is the preferred template.

As provided herein an amplification enzyme is any enzyme which can be used for in vitro nucleic acid amplification, e.g. by the above-described procedures. Such amplification enzymes include *Escherichia coli* DNA polymerase I, Klenow fragment of *E. coli* DNA polymerase I, T4 DNA polymerase, T7 DNA polymerase, *Thermus aquaticus* DNA polymerase, *Thermococcus litoralis* DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Qβ replicase.

The preferred oligonucleotides for the present amplification methods include oligonucleotides which can hybridize to the *M. hominis* DNA inserts of pMhom120, pMh5 or the *M. hominis*-specific fragments thereof. In one embodiment, oligonucleotides each have a nucleotide sequence with at least about 70% homology to at least 14 contiguous bases of either strand of SEQ ID NO:1. Preferred oligonucleotides have at least about 80%, and more preferably 90%, sequence homology to at least about 14 contiguous nucleotides of SEQ ID NO:1.

Moreover the present oligonucleotides for use in in vitro nucleic acid amplification can produce copies of a *M. hominis* nucleic acid target but produce detectably fewer or no copies of a non-*M. hominis* target nucleic acid, e.g. from *U. urealyticum* or genomic DNA from the the non-*M. hominis* Mycoplasm species listed herein.

Especially preferred oligonucleotides have any one of SEQ ID NOS:4–7. When two oligonucleotides are employed, preferred oligonucleotides have SEQ ID NO:5 and SEQ ID NO:6. For example, when oligonucleotides havaing SEQ ID NO:5 and 6 are employed in a PCR reaction copies of a 152 bp fragment corresponding to positions 105–256 of SEQ ID NO:1, inclusive, are obtained. Any of these oligonucleotides can have additional sequences which encode an RNA polymerase recognition site or a Qβ replicase recognition site in the configuration necessary to practice in vitro nucleic acid amplification.

As used herein a sample can be a mammalian body fluid, secretion or tissue, as well as a culture or a transport medium. Such mammalian samples can be collected from, for example, humans, domestic animals, farm animals and pets. As used herein mammals also include adult, neonate and infant patients. Samples can be collected by procedures known to the skilled artisan, e.g. by requesting or collecting urine, fecal and semen samples, by swabbing for throat, urethral, vaginal and nasal samples, by aspirating for tracheal samples, by withdrawing blood and amniotic fluid samples, and by obtaining tissue biopsies.

According to the present invention, mammalian body fluids include blood, urine, semen, vaginal secretions, amniotic fluid, saliva, mucus, pulmonary fluids and the like. Especially useful body fluids include mucus, urine, semen, vaginal secretions, amniotic fluid, saliva and pulmonary fluids. Animal secretions include fecal matter.

As used herein mammalian tissues include tissues such as lung, bronchial and urogenital tissues. Urogenital tissues include tissues obtained during medical procedures, especially urethral, bladder, kidney, prostatic, vaginal, cervical, uterine and similar tissues.

As provided herein, culture media includes any solution for growth of a prokaryotic or eukaryotic cell. Similarly, transport medium samples include solutions for transport of a prokaryotic or eukaryotic cell, but can also include solutions used during transport of a mammalian body fluid, secretion, or tissue.

In another embodiment, the present oligonucleotides, nucleic acids and methods can be used to detect *M. hominis* contamination in cultured eukaryotic cells or tissues, separately or in conjunction with known tests for detection of Mycoplasma contamination.

Furthermore, the present oligonucleotides, nucleic acids and methods can be used in conjunction with available oligonucleotides, nucleic acids and methods used for detection of other Mycoplasm. For example, applicants U.S. patent application Ser. No. 07/874,842 by DelVecchio et al., which was abandoned in favor of U.S. patent application Ser. No. 08/228,913, discloses oligonucleotides, nucleic acids and methods for detection of *U. urealyticum*. As provided herein the present *M. hominis*-specific oligonucleotides, nucleic acids and methods can be used in conjunction with those provided in U.S. patent application Ser. No. 07/874,842.

Detection of the amplified *M. hominis* target nucleic acid (i.e. the RNA or DNA copies of the target) can be accomplished by conventional gel electrophoretic or nucleic acid hybridization techniques. Gel electrophoretic techniques permit identification of a nucleic acid having a specific size which is diagnostic of *M. hominis* infection. For example, according to the present invention oligonucleotides having SEQ ID NO:5 and 6 can be used for in vitro amplification of an *M. hominis*-specific nucleic acid having 152 bp (i.e. SEQ ID NO:3). Further, according to the present invention, detection of such a 152 bp fragment is diagnostic of *M. hominis* infection.

Nucleic acid hybridization techniques include solid-phase-based hybridization and solution hybridization using a variety of reporter molecules. Detailed methodology for gel electrophoretic and nucleic acid hybridization techniques can be found in Sambrook et al., Diamandis et al. (1990) *Clin. Chim. Acta.* 194:19–50; Landegren et al. (1988) *Science* 242:229–237; Wolcott et al. (1991) *J. Food Protect.* 54:387–401 and as further described hereinbelow.

Another aspect of this invention provides a method of detecting *Mycoplasma hominis* which includes contacting a sample to be tested for the presence of an *M. hominis* target nucleic acid with a nucleic acid probe for a time and under conditions sufficient to permit hybridization between the nucleic acid probe and the *M. hominis* target nucleic acid and detecting or measuring the hybridization; wherein the nucleic acid probe includes a nucleotide sequence selected from genomic *M. hominis* DNA such that the probe is sufficiently complementary to hybridize to the target nucleic acid and wherein the probe does not hybridize to genomic DNA of *U. urealyticum*, *M. genitalium*, *M. hyorhinis*, *M. orale*, *M. pneumoniae* or *M. salivarium*. Preferably the nucleic acid probe is selected from genomic *M. hominis* DNA which does not encode 16S ribosomal RNA.

In a preferred embodiment the nucleic acid probe includes a nucleotide sequence of at least about 14 nucleotides which hybridizes to SEQ ID NO:1. More preferred nucleic acid probes of the present invention are the *M. hominis* DNA inserts in pMhom120, pMh5 and nucleic acids probes which are sufficiently complementary to hybridize to target nucleic acids containing these sequences. More particularly, preferred nucleic acid probes have SEQ ID No:1, SEQ ID NO:3, SEQ ID NO:4, SEQ ID NO:5, SEQ ID NO:6, SEQ ID NO:7 or mutations and variations of these sequences which are sufficiently complementary to detect a target nucleic acid having SEQ ID NO:1. Moreover the preferred isolated nucleic acid can hybridize to the *M. hominis* DNA in pMhom120, e.g. a nucleic acid including SEQ ID NO:1, but undergoes little or no detectable hybridization to genomic DNA of *U. urealyticum, M. genitalium, M. hyorhinis, M. orale, M. pneumoniae* or *M. salivarium*.

Nucleic acid hybridization as used herein includes solid phase-based hybridization (heterogeneous methods), solution phase hybridization (homogeneous methods) and in situ hybridization. All these methods are known to the skilled artisan and readily modified for use with the subject *M. hominis*-specific probes. There are many variations on these techniques which are known to the skilled artisan and which are included herein; many of these techniques are described, for example, by Sambrook et al., Diamandis et al., Landegren et al. and Wolcott et al.

The samples for use in the present method of nucleic acid hybridization to detect *M. hominis* are the same as those described to detect *M. hominis* using in vitro nucleic acid amplification.

Detection of *M. hominis*, whether or not amplification of the target has been done, can be by any of a variety of hybridization techniques which are known in the art. Such techniques include Southern and Northern hybridization to RNA or DNA obtained from clinical samples, and in situ hybridization to tissues or cells which may be infected by *M. hominis*. Methods for performing these techniques are available, for example, in Sambrook et al.

*M. hominis* can be detected in sample nucleic acids which have or have not undergone purification. For example, RNA or DNA can be extracted from samples using techniques available in the art, then immobilized onto nitrocellulose or nylon filters, and well-known filter hybridization techniques may be employed for detection of *M. hominis* nucleic acids. However, sample nucleic acids need not be purified. For example, sample cells can simply be lysed and cellular RNA or DNA fixed unto a filter. Sample RNA and DNA can also be size fractionated through a gel before fixation onto a filter, or simply dot blotted unto a filter.

In situ hybridization can be performed by procedures known in the art, for example as disclosed in Gall et al. (1969) *Proc. Natl. Acad. Sci. USA* 63:378–83; Giovannoni et al. 1988 *J. Bacteriol.* 170:720–726; or DeLong et al. (1990) *Diag. Clin. Test.* 28:41–44.

According to the present invention, a probe of the subject isolated nucleic acids, nucleic acid probes or oligonucleotides of the present invention, can be labelled by any procedure known in the art, for example by incorporation of nucleotides linked to a "reporter molecule".

A "reporter molecule" as used herein, is a molecule which provides an analytically identifiable signal allowing detection of a hybridized probe or an antibody-antigen complex. Detection may be either qualitative or quantitative. Commonly used reporter molecules include fluorophores, enzymes, biotin, chemiluminescent molecules, bioluminescent molecules, digoxigenin, avidin, streptavidin or radioisotopes. Fluorophores that are readily available and suitable for the methods of the present invention include fluorescein isothiocyanate (FITC), rhodamine red and the like. Commonly used enzymes include horseradish peroxidase, alkaline phosphatase, glucose oxidase and β-galactosidase, among others. Enzymes can be conjugated to avidin or streptavidin for use with a biotinylated probe. Similarly, nucleic acids, antigens or antibodies can be conjugated to avidin or streptavidin for use with a biotinylated enzyme. The substrates to be used with these enzymes are generally chosen for the production, upon hydrolysis by the corresponding enzyme, of a detectable color change. For example, p-nitrophenyl phosphate is suitable for use with alkaline phosphatase reporter molecules; for horseradish peroxidase, 1,2-phenylenediamine, 5-aminosalicyclic acid or tolidine are commonly used.

Reporter molecules which can directly provide an analytically identifiable signal include, e.g. a fluorophore, a chemiluminescent molecule, a bioluminescent molecule, a radioisotope and the like. However reporter molecules can also be detected by addition of another reagent, e.g. by adding a substrate for an enzyme reporter molecule, by binding an antibody conjugated to an enzyme or other reporter molecule, and the like. For example, a digoxigenin reporter molecule can be detected by binding an anti-digoxigenin antibody which has conjugated thereto a second reporter molecule, e.g. an enzyme. The antibody-conjugated enzyme is then detected by application of a substrate for the enzyme.

Incorporation of a reporter molecule into DNA can be by any method known to the skilled artisan, for example by nick translation, primer extension, random oligo priming, by 3' or 5' end labeling or by other means (see, for example, Sambrook et al.).

Incorporation of a reporter molecule into RNA can be by synthesis of *M. hominis*-specific RNA using T3, T7, Sp6 or other RNA polymerases (Sambrook et al.). Such enzymes require an *M. hominis*-specific DNA template having the appropriate RNA polymerase start signals at sites flanking the template. These start signals can be juxtaposed to the DNA template by insertion of a DNA template for the probe into a vector having start signals flanking the insertion site. Suitable vectors having such start signals include pGEM (Promega Biotec), pBluescript (Vector Cloning Systems), pSP6 (Bethesda Life Technologies), Gene Scribe® (U.S. Biochem. Corp.) and related vectors.

In a preferred embodiment, in situ hybridization is performed on sample body fluids such as blood, urine, amniotic fluid, semen, vaginal secretions and pulmonary fluid. Clinical specimens of these fluids are obtained and cellular and microbial material is sedimented. Cell smears can be prepared on a standard microscope slide, then fixed with an appropriate fixative. The labeled probe then is applied to the slide and slides are incubated at a suitable hybridization temperature (generally 15° to 55° C.) for 1–20 hours. Non-hybridized probe is then removed by extensive, gentle washing at an appropriate stringency.

When a fluorescent reporter molecule is used, the slide is mounted in an appropriate medium, such as SAVA mounting fluid, and the fluorescence is observed under a fluorescent microscope. If an enzyme is used as a reporter molecule, a suitable substrate or substrates are applied. The slide can then be incubated at an appropriate temperature for a time appropriate to allow a detectable color signal to appear when the slide is examined by light microscopy. Alternatively, if the probe is radioactively labeled, hybridized slides can be dipped in photoemulsion. After a suitable exposure time, the slides can be developed and the signal detected as visible silver-grains under the light microscope.

In yet a further aspect, the present invention provides a compartmentalized kit for detection of *M. hominis*. This kit can be adapted to facilitate detection by a method involving a first step of in vitro nucleic acid amplification followed by detecton of the amplified fragment or by a method of nucleic acid hybridization in accordance with the invention. The kit has a receptacle containing at least one of the present isolated nucleic acids or oligonucleotides.

In this regard the kit receptacle can contain an isolated nucleic acid specific for *M. hominis* including pMhom120, pMh5 or *M. hominis*-specific fragments thereof. Likewise the kit receptacle can contain any isolated nucleic acid having a nucleotide sequence of at least about 14 nucleotides which is at least about 70% homologous to either strand of the *M. hominis* DNA insert in plasmid pMhom120. In a more preferred embodiment such isolated nucleic acids are at least about 70% homologous to either strand of SEQ ID NO:1. Moreover such isolated nucleic acids can hybridize to a nucleic acid including the *M. hominis* DNA insert in plasmid pMhom120, or preferably SEQ ID NO:1, and can not hybridize to genomic DNA of *U. urealyticum, M. genitalium, M. hyorhinis, M. orale, M. pneumoniae* or *M. salivarium*. For example, such an isolated nucleic acid can comprise a nucleotide sequence of SEQ ID NO:1, SEQ ID NO:3, or any one of SEQ ID NOS:4–7.

When the kit is used for in vitro amplification, the preferred nucleic acids include at least one oligonucleotide. Kits designed for PCR preferably include two oligonucleotides as isolated nucleic acids, e.g. either SEQ ID NO:4 and SEQ ID NO:7 or SEQ ID NO:5 and SEQ ID NO:6. An especially preferred pair of oligonucleotides for PCR have the sequence of SEQ ID NO:5 and of SEQ ID NO:6. When the kit is used for nucleic acid detection by hybridization, a probe having the sequence of SEQ ID NOS:1 or 3–7, is preferably included.

The kit can also be adapted to contain another receptacle having an *M. hominis* nucleic acid at a known concentration to act as a standard or positive control. Suitable *M. hominis* nucleic acids for use as standards or positive controls include any of the present oligonucleotides or isolated nucleic acids, *M. hominis* genomic DNA, mRNA, rRNA, tRNA or the like. A preferred standard or positive control is *M. hominis* genomic DNA, an isolated DNA having SEQ ID NO:1 or SEQ ID NO:3 or pMhom120.

The kit can be further adapted to contain another receptacle having any available nucleic acid for detection of another Mycoplasma species, e.g. *U. urealyticum*. In this regard applicants U.S. patent application Ser. No. 07/874,842 by DelVecchio, which was abandoned in favor of U.S. patent application Ser. No. 08/228,913, discloses nucleic acids and oligonucleotides for detection of *U. urealyticum*. For example, the present kits can include at least one a receptacle which contains *U. urealyticum*-specific nucleic acids having any one of SEQ ID NO: 8–16.

The compartmentalized kit can also include another receptacle containing a reagent for synthesis of the DNA or RNA by in vitro nucleic acid amplification. For example, such a reagent can be an amplification enzyme or a mixture of nucleotides and can include any salts and cofactors required by the enzyme for synthesis of the DNA or RNA segment. Some of the amplification enzymes contemplated by the present invention for synthesis of DNA or RNA include *E. coli* DNA polymerase I, Klenow fragment of *E. coli* DNA polymerase I, T4 DNA polymerase, T7 DNA polymerase, *T. aquaticus* DNA polymerase, *T. litoralis* DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Qβ replicase.

The compartmentalized kit can also have further receptacle containing a reagent for detection of a reporter molecule. Such a reagent can be, e.g. an antibody or a substrate for an enzyme.

Another aspect of the present invention provides an expression vector including any of the present *M. hominis* nucleic acids wherein the nucleic acid is operably linked to a segment of the vector which can effect expression, i.e. transcription and/or translation, of the nucleic acid. Such an expression vector allows regulated expression of the present polypeptides. For example, such an expression vector can include the *M. hominis* DNA in pMhom120 or an isolated nucleic acid including SEQ ID NO:1 or SEQ ID NO:3.

Expression vectors as described herein are generally DNA molecules engineered for controlled expression of a desired gene, especially high level expression where it is desirable to produce large quantities of a particular RNA or gene product (polypeptide). The vectors encode promoters and other sequences to control expression of the gene being expressed, and can encode an origin of replication which is operable in the contemplated host. The present vectors can also contain sequences which are transcribed with the present isolated nucleic acids and which contain signals for translation of a polypeptide encoded by the present nucleic acids. Preferably expression vectors are plasmids, bacteriophages, cosmids or viruses. Any expression vector comprising RNA is also contemplated.

Elements included within the vector which can effect expression of a gene product include promoters, enhancer elements, transcription termination signals, polyadenylation sites, translation start signals and the like.

Promoters are DNA sequence elements for controlling gene expression, in particular, promoters specify transcription initiation sites. Control of gene expression includes the ability to regulate a gene both positively and negatively (i.e., turning gene expression on or off) to obtain the desired level of expression. Any available promoter or variation of an available promoter including, e.g. a genetically-engineered promoter, is contemplated herein.

Prokaryotic promoters that are contemplated by the present invention include, for example, the lac promoter, the trp promoter, the $P_L$ and $P_R$ promoters of lambda, the T7 polymerase promoter, the T3 polymerase promoter, the Sp6 polymerase promoter and the like. Eukaryotic promoters include promoters of viral origin, such as the baculovirus polyhedrin promoter, the vaccinia virus hemagglutinin (HA) promoter, SV40 late promoter, the Moloney Leukemia Virus LTR, and the Murine Sarcoma Virus (MSV) LTR. Yeast are also contemplated.

Translational start signals include a ribosomal binding site and an initiation codon.

One skilled in the art has available many choices of expression vectors, compatible hosts and well-known methods for making and using the vectors. Recombinant DNA methods are found in any of the myriad of standard laboratory manuals on genetic engineering (see for example Sambrook et al., 1989, *Molecular Cloning: A Laboratory Approach*, 2nd edition, Cold Spring Harbor Laboratory Press, Cold Spring Harbor, N.Y.).

Insertion of an isolated DNA into an expression vector can be by ligation, in the sense or antisense orientation, to the vector segment which can effect transcription of a RNA copy of the isolated DNA. When the transcribed RNA is a sense RNA the encoded polypeptide can then be synthesized within a host cell. For example, a DNA fragment encoding nucleotides 3–470 of SEQ ID NO:1 can be operably linked by ligation to a promoter, thereby allowing expression of a 157 amino acid polypeptide having SEQ ID NO:2. This juxtapositioning of promoter and other sequence elements with a polypeptide coding region allows the production of large amounts of polypeptide.

Preferred vectors of the present invention are derived from prokaryotic sources, including bacterial and bacteriophage vectors that can transform such hosts as E. coli, B. subtilis, Streptomyces sps. and other microorganisms. Many of these vectors are based on pBR322 including pUC19 and pGEM-7Zf (commercially available from Promega, Madison, Wis.) and are well known in the art. Bacteriophage vectors that are used in the invention include lambda and M13.

The present invention also contemplates eukaryotic vectors that are suitable as cloning vectors or as expression vectors for M. hominis polypeptides. Expression vectors that function in tissue culture cells are especially useful, but yeast vectors are also contemplated. These vectors include yeast plasmids and minichromosomes, retrovirus vectors, BPV (bovine papilloma virus) vectors, vaccinia virus vectors, baculovirus vectors, SV40 based vectors and other viral vectors. Baculovirus vectors and retrovirus vectors (e.g., murine leukemia viral vectors) are also contemplated. Tissue culture cells that are used with eukaryotic replicable expression vectors include S. frugiperda cells, VERO cells, MRC-5 cells, SCV-1 cells, COS-1 cells, NIH3T3 cells, mouse L cells, HeLa cells and such other cultured cell lines known to one skilled in the art.

In one embodiment an isolated DNA encoding a polypeptide with an amino acid sequence including SEQ ID NO:2 is inserted into a lambda gt11 expression vector (Sambrook et al., 1989, *Molecular Cloning: A Laboratory Manual* Vol. 2, Cold Spring Harbor Laboratory Press: 12.1–12.44). Lambda gt11 is constructed to allow insertion of M. hominis DNA into the structural gene for beta-galactosidase, thereby producing a beta-galactosidase-M. hominis protein fusion, under the control of the lac promoter. Such a fusion protein is easily isolated, for example, by using commercially available anti-beta-galactosidase antibodies. The fusion protein can be used to generate antibodies against the M. hominis polypeptide.

As an alternative prokaryotic expression system, the pKK223-3 expression vector, can provide high levels of polypeptide expression in E. coli. This vector contains the strong trp-lac (tac) promoter which is IPTG inducible. (deBoer et al., 1983, Proc. Natl. Acad. Sci. USA). A major advantage of the pKK223-3 expression vector is that a non-fusion polypeptide is expressed rather than a beta-galactosidase fusion protein.

A further aspect of the present invention is directed to an isolated polypeptide having an M. hominis-specific amino acid sequence, e.g. SEQ ID NO:2. In one embodiment the present invention is directed to a polypeptide including at least six contiguous amino acids of SEQ ID NO:2. Such a polypeptide or peptide can be employed as a antigen or vaccine against M. hominis and for production of anti-M. hominis-specific antibodies.

An isolated polypeptide of the present invention can be obtained from cultured M. hominis cells, from M. hominis-infected animals or from a host cell containing an expression vector encoding an M. hominis-specific polypeptide, e.g. a polypeptide whose amino acid sequence includes SEQ ID NO:2.

In another embodiment, the present invention provides a process for producing one of the present polypeptides, e.g. a polypeptide having a sequence comprising SEQ ID NO:2, by cultivating one of the instant host cells for a time and under conditions sufficient to produce the polypeptide.

Purification of the present polypeptides, whether from cultured M. hominis or from a recombinant host cell containing a nucleic acid encoding such a polypeptide, is achieved by conventional purification techniques known to the skilled artisan. Such procedures can include ammonium sulfate precipitation, column chromatography, affinity chromatography and the like. During purification, the M. hominis polypeptide can be identified by SDS-polyacrylamide gel electrophoresis as a protein not normally present in the host cell, or by standard immunodetection techniques, such as immunoblotting or immunoprecipitation.

Antibodies can be used to purify the present M. hominis polypeptides including polypeptides whose sequence includes SEQ ID NO:2. As is known to the skilled artisan, antibodies are highly specific and are especially useful for isolating specific antigens (polypeptides) that are present as only minor components of complex mixtures such as cell lysates.

The lambda gt11 expression system described above provides a fusion protein of beta-galactosidase and a polypeptide whose sequence can, for example, include SEQ ID NO:2. This fusion protein can be purified by passage of a cell lysate containing the fusion protein over an anti-beta-galactosidase immunoaffinity column. The anti-beta-galactosidase antibodies bound to the column matrix bind the fusion protein. Any impurities can be washed off the column and the fusion protein can be eluted by changes in pH, or by use of detergents, chaotropic agents or organic solvents. Immunoaffinity purification techniques are well known in the art (see, for example, Harlowe, et al., 1988, *Antibodies: A Laboratory Manual,* Cold Spring Harbor Labortory Press: 511–552).

The purified fusion protein can be used to obtain antibodies specific for M. hominis and reactive with a polypeptide whose sequence includes SEQ ID NO:2. These antibodies in turn allow immunoaffinity purification of non-fusion polypeptides or peptides having a sequence which includes a portion of SEQ ID NO:2.

Another embodiment of the present invention provides polyclonal or monoclonal antibodies directed against a polypeptide having a sequence including SEQ ID NO:2 or against an M. hominis peptide including at least about 6 amino acids of SEQ ID NO:2. As is known to the skilled artisan a peptide of at least about six amino acids can produce antibodies specific to that peptide (see Harlow et al. p. 75–76).

According to the present invention such a peptide can be used to produce antibodies reactive with M. hominis. When the present peptides are utilized to produce antibodies the peptide is preferably an antigenic peptide and more preferably raises an immune response against M. hominis. Further, the present antigenic polypeptides and peptides preferably have at least one M. hominis-specific epitope. The antibodies are useful for detection of M. hominis and for purification of the present polypeptides.

Computer analysis of a polypeptide amino acid sequence, e.g. SEQ ID NO:2, can be used to identify peptide sequences as being strongly antigenic epitopes. As is known to the skilled artisan strongly antigenic epitopes include regions of a polypeptide having a potential for being an exposed domain at the surface of the polypeptide. Such regions frequently include clusters of hydrophilic amino acids and can be identified by computer analysis. For example, the program of Jameson and Wolf (Jameson et al. 1988 CABIOS 4: 181–186) can be used to predict highly immunogenic regions of a polypeptide from its amino acid sequence. Such computer programs are commercially available.

After selection of an immunogenic or antigenic peptide, such a peptide can be synthesized by known techniques, for example by either solution or solid phase synthetic procedures such as the Merrifield procedure. Solid phase synthesis is commonly preferred for making peptides having six or more amino acids. General procedures for peptide synthesis are provided in Barany et al. (1980, in *The Peptides* 2: 1–284, Gross E. and Meienhofer, J. eds, Academic Press, New York) and Stewart et al. (*Solid Phase Peptide Synthesis,* Pierce Chemical Co.). Peptides can also be made commercially.

The following peptides are preferred antigens for generating antibodies:

Polyclonal antibodies directed against the subject polypeptides or peptides, are prepared by injection of a suitable animal with an immunogenic amount of the polypeptide or the peptide, collecting serum from the animal, and testing sera for the desired reactivity. If necessary, specific sera can be isolated by any of the known immunoadsorbent techniques. Detailed protocols for antibody production are provided in Harlow, E. et al. *Antibodies: A Laboratory Manual,* Cold Spring Harbor Press, N.Y., 1988.

Another embodiment of the present invention provides monoclonal antibodies. Monoclonal antibodies are preferred because large quantities of antibodies, all of similar reactivity, are produced. The preparation of hybridoma cell lines for monoclonal antibody-production is done by fusing an immortal cell line with antibody-producing lymphocytes from an immunized animal. This can be done by techniques which are well known to those who are skilled in the art. (See, for example, Harlow, E. and Lane, D., *Antibodies: A Laboratory Manual,* Cold Spring Harbor Press, 1988; or Douillard, J. Y. and Hoffman, T., "Basic Facts About Hybridomas", in *Compendium of Immunology Vol. II,* L. Schwartz (Ed.), 1981.)

Unlike the preparation of polyclonal sera, the choice of animal for monoclonal antibody preparation is dependent on the availability of appropriate immortal cell lines capable of fusing with the antibody-producing lymphocytes derived from the immunized animal. Mouse and rat have been the animals of choice for hybridoma technology and are preferably used. For the purpose of making the monoclonal antibodies of the present invention, the animal of choice may be injected with from about 0.01 mg to about 20 mg of antigen, e.g. purified polypeptide whose sequence includes SEQ ID NO:2, or an antigenic peptide thereof.

The antigen can be emulsified in an adjuvant to stimulate general immune responses. Boosting injections are generally also required. Lymphocytes can be obtained by removing the spleen or lymph nodes of immunized animals in a sterile fashion, and are fused to immortalized cells. A number of immortalized cell lines suitable for fusion have been developed, and the choice of any particular line is directed by any one of a number of criteria such as speed, uniformity of growth characteristics, deficiency of its metabolism for a component of the growth medium, and potential for good fusion frequency. Intraspecies hybrids, particularly between like strains, work better than interspecies fusions. Several cell lines are available, including mutant selected for the loss of ability to create myeloma immunoglobulin. Included among these are the following mouse myeloma lines: X63-Ag 8.653, MPC11-X45-6TG, P3 NS1/1-Ag4-1, P3-X63-Ag14 (all BALB/C derived), Y3'Agl.2.3 (rat), and U266 (human).

The fused cell colonies are tested for the presence of antibodies that recognize the antigen, e.g. a polypeptide whose sequence includes SEQ ID NO:2, or a peptide thereof. Detection of monoclonal antibodies can be performed using any immunoassay assay, e.g. an assay where the antigen is bound to a solid support and allowed to react to hybridoma supernatants which may contain antibodies. Most of the common methods are sufficiently sensitive for use in the range of antibody concentrations secreted during hybrid growth.

Cloning of hybrid cells can be carried out after 20–25 days of cell growth in selected medium. Cloning can be performed by cell limiting dilution in fluid phase or by directly selecting single cells for growth in semi-solid agarose. Cell limiting dilution procedures involve serially diluting cell suspensions to a dilution where there is a statistical probability of having only one cell per well. When using agarose, cell hybridomas are seeded in a semisolid upper layer of agarose, which is placed upon a lower agarose layer containing feeder cells. After cell growth, hybridoma colonies from the upper layer are transferred to individual wells.

Antibody-secreting hybrid cells can be grown in various tissue culture flasks, yielding supernatants with variable concentrations of antibodies. In order to obtain higher concentrations, hybrid cells can be transferred into animals by intraperitoneal injection to obtain inflammatory ascites. Antibody-containing ascites can be harvested 8–12 days after injection. The ascites contain a higher concentration of antibodies but include both monoclonals and immunoglubulins from the inflammatory ascites. Antibodies can be achieved by known prcedures, e.g. affinity chromatography.

Antibodies raised against an isolated polypeptide or peptide of the present invention, can be screened for *M. hominis*-specificity by observing whether such antibodies also react with *U. urealyticum, M. genitalium, M. hyorhinis, M. orale, M. pneumoniae* or *M. salivarium.* Antibodies which can detectably distinguish *M. hominis* from the afore-mentioned Ureaplasm and non-*M. hominis* Mycoplasm species by any available immunoassay, are *M. hominis*-specific.

A further embodiment of the present invention is directed to a method for detecting *M. hominis* by contacting a test sample with an antibody which has been rasied against, or is reactive with, one of the present *M. hominis*-specific polypeptides for a time and under conditions sufficient to form a polypeptide-antibody complex, and detecting the complex.

As used herein conditions for detecting *M. hominis* include a physiological buffer and temperature appropriate for performing an immunoassay. In general a temperature of about 4° C. to about 37° C. is preferred. Physiological buffers are known to the skilled artisan, e.g. phosphate buffered saline (PBS) and the like.

The time required for detecting *M. hominis* is that amount of time which allows detectable binding to occur between the antigen and antibody. The incubation period can vary but generally is in the range of about 5 minutes to 16 hours.

For example, the presence of an *M. hominis* can be detected utilizing either monoclonal or polyclonal antibodies prepared as described above in virtually any type of immunoassay. The skilled artisan is cognozant of a wide range of immunoassay techniques, as can be seen by reference to Harlow, et al. (*Antibodies: A Laboratory Manual*, Cold Spring Harbor Press, 1988) and U.S. Pat. Nos. 4,018, 043 and 4,424,279.

Immunoassays contemplated by the present invention include both single-site and two-site assays, non-competitive sandwich assays and competitive binding assays. Sandwich assays are among the most useful and commonly used assays. A number of variations of the sandwich assay technique exist, and all are intended to be encompassed by the present invention. Briefly, in a typical forward assay, an unlabeled primary antibody is immobilized on a solid substrate and the sample to be tested is brought into contact with the primary antibody. After a suitable time of incubation allowing formation of an antibody-antigen binary complex, a secondary antibody is then added. The secondary antibody is generally labeled with a reporter molecule capable of producing a detectable signal. A second incubation permits formation of a ternary complex of primary antibody-antigen-secondary antibody. Any unreacted material is washed away, and the presence of the antigen is determined by observation of a signal produced by the reporter molecule. The results may either be qualitative, by simple observation of the visible signal, or may be quantitated by comparison with a control sample containing known amounts of antigen. Variations on the forward assay include a simultaneous assay, in which both the sample to be tested and the secondary antibody are first combined, incubated and then added to the unlabeled bound primary antibody. These techniques are well known to those skilled in the art; further variations readily apparent to such a skilled artisan. As used herein, "sandwich assay" is intended to encompass all variations on the basic two-site technique.

The present *M. hominis* polypeptides can also be detected by a competitive binding assay in which a limiting amount of antibody specific for the present polypeptides is combined with a sample containing an unknown amount of the *M. hominis* polypeptide. A known amount of labeled *M. hominis* polypeptide is also present in the assay mixture. Labeled and unlabeled polypeptides then compete for the available antibodies. Phase separation of the free and antibody-bound molecules allows measurement of the amount of label present in each phase, thus indicating the amount of polypeptide in the sample being tested. Numerous variations on this general competitive binding assay, are known to the skilled artisan and are contemplated by the present invention.

An antibody or an antigenic polypeptide of the present invention, can be bound to a solid surface. The solid surface is typically glass or a polymer, the most commonly used polymers being cellulose, polyacrylamide, nylon, polystyrene, polyvinyl chloride or polypropylene. The solid support may be in the form of tubes, beads, discs or microplate, or any other surface suitable for conducting an immunoassay. The binding processes are well-known in the art and generally consist of cross-linking, covalently binding or physically adsorbing the molecule to the insoluble carrier. Following binding, the solid support-antibody or solid support-antigen should be washed prior to performing the immunoassay.

In another embodiment, antibodies directed against the present *M. hominis* polypeptides or antigenic peptides are incorporated into a kit for the detection of *M. hominis* infection. Such a kit can encompass any immunoassay detection system including the assays described herein, and can employ either polyclonal or monoclonal antibodies directed against the present *M. hominis* polypeptides, e.g. a polypeptide having a sequence including SEQ ID NO:2, or an antigenic peptide thereof. Both antibodies complexed to a solid surface described above or soluble antibodies are contemplated for use in a detection kit.

The kit can be compartmentalized and includes at least one receptacle containing a primary antibody reactive with one of the present *M. hominis* polypeptides or peptides. The antibodies provided in the present kits are *M. hominis*-specific, e.g. raised or directed against a polypeptide having a sequence including SEQ ID NO:2. Another receptacle can also be included in the kit which contains secondary antibodies covalently bond to a reporter molecule. Such a secondary antibody can react either with the polypeptide or with the primary antibody. The kit can further contain a standard or a positive control, e.g. killed *M. hominis* or an isolated polypeptide whose sequence includes SEQ ID NO:2. An additional receptacle can include a substrate, or reagent, appropriate for visualization of the reporter molecule.

Another embodiment of the present invention provides pharmaceutical compositions containing any one of the present isolated *M. hominis* polypeptides or peptides. For example the present invention provides a antigenic composition which includes one of the present polypeptides or peptides and a pharmaceutically acceptable carrier. Preferred polypeptides and peptides include at least about 6 amino acids of SEQ ID NO:2.

A further embodiment of the present invention provides a vaccine composition which includes an immunogenic amount of one of the present *M. hominis* polypeptides or peptides and a pharmaceutically acceptable carrier.

An effective dosage of the present compositions is about 0.5 μg to about 2000 mg of antigen per kilogram of body weight. Boosting regiments may be required and the dosage regimen can be adjusted to provide an optimal immunological response. Compositions can be administered parenterally, or extra-parenterally to the mucosal surfaces of the body. The intramuscular route of innoculation is preferred.

The compositions of the present invention can be administered in a variety of forms adapted to the chosen route of administration, e.g., oral, topical, intradermal, intravenous, intramuscular, intraperitoneal or subcutaneous routes. The subject compositions can also be administered parenterally by osmotic pump to permit continuous infusion of the antigen, for example, as described in Rataiczak et al.. (1992 Proc. Natl. Acad. Sci. USA 89: 11823–11827). Such osmotic pumps are commercially available, e.g., from Alzet, Inc (Palo Alto, Calif.).

For oral administration the present compositions can be protected, e.g., by enclosure in hard or soft shell gelatin capsules. For oral therapeutic administration, the composition can be incorporated with excipient and used in the form of ingestible tablets, buccal tablets, troches, capsules, elixirs, suspensions, syrups, wafers, incorporated directly with the food of the diet and the like. The composition can be incorporated into liposomes or liposomes modified with polyethylene glycol for parenteral administration.

The amount of antigen in such therapeutically useful compositions is varied such that a suitable dosage will be obtained. Compositions according to the present invention are prepared in unit dosage form so that an oral dosage unit form contains an amount ranging from about 0.01 mg to about 1 g of antigen. Preferred dosage ranges from about 0.01 mg to about 500 mg of antigen.

The composition can also be administered parenterally. Solutions of the antigen can be prepared in water and mixed with a surfactant such as hydroxypropylcellulose or a dispersing agent such as glycerol, a liquid polyethylene glycol, an oil and a mixture thereof.

The pharmaceutical forms suitable for injection include sterile aqueous solutions or dispersions and sterile powders for the extemporaneous preparation of sterile injectable solutions or dispersions. In all cases the form must be sterile and preserved against the contaminating action of microorganisms such as bacteria and fungi. Such pharmaceutical forms for injection must be fluid to the extent that easy syringability exists. Preferably the pharmaceutical composition is stable under the conditions of manufacture and storage.

A pharmaceutical carrier can be a solvent or dispersion medium containing, for example, water, ethanol, polyol (for example, glycerol, propylene glycol, polyethylene glycol and the like), vegetable oil and suitable mixtures thereof. The proper fluidity can be maintained, for example, by the use of a coating such as lecithin, by the maintenance of the required particle size in the case of dispersion and by the use of surfactants. Isotonic agents, for example, sugars, potassium chloride or sodium chloride can be included in the vaccine. Prolonged absorption of the injectable compositions can be achieved by including agents which delay absorption, for example, aluminum monostearate and gelatin.

Sterile injectable solutions are prepared, for example, by filter or heat sterilization. Dispersions which do not lend themselves to filtration can be prepared by incorporating the various sterilized active ingredients into a sterile vehicle or carrier. Powders for the preparation of sterile injectable solutions, can be prepared by vacuum drying or freeze-drying sterile solutions of the appropriate antigen in a vehicle or carrier.

As used herein, "pharmaceutically acceptable carrier" includes solvents, dispersion media, coatings, antibacterial agents, antifungal agents, isotonic agents, absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The examples further illustrate the invention.

EXAMPLE 1

MATERIALS AND METHODS

Bacterial strains

The following species of Mycoplasma were obtained from the American Type Culture Collection (Rockville, Md.): *M. hominis* ATCC 23114, *M. orale* ATCC 23714, *M. genitalium* ATCC 33530, *M. pneumoniae* ATCC 15531, *M. salivarium* ATCC 33130, *M. hyorhinis* ATCC 23839, *Ureaplasma diversium* ATCC 43321 and *Ureaplasma urealyticum* ATCC 27618,. Growth media and culture conditions were as described by Velleca et al. (1980) Laboratory Diagnosis of Mycoplasma Infections, Center for Disease Control, Atlanta, pp. 111≅122.

*Eschericihia coli* strain DH5α (Gibco BRL, Bethesda, Md.) was used as a host in cloning experiments.

Clinical Samples

Clinical samples were obtained by standard methods [Walsh et al. (1991) *Pediatr. Infect. Dis. J.* 10:823–827] from patients admitted to Wilford Hall USAF Medical Center, San Antonio, Tex., and David Grant Medical Center, Travis Air Force Base, Fairfield, Calif. Samples were from respiratory tract infections of neonates in the form of throat swabs, blood samples, tracheal aspirants and lung biopsies. Adult urethral swabs, vaginal swabs and placental tissue were also obtained. Specimens were shipped in Mycotrans (Irvine Scientific, Santa Ana, Calif.).

Mycoplasma and Ureaplasma isolates were grown in Mycotrim GU media (Irvine Scientific). Remel Arginine broth and Remel 10B medium were used to test for the presence of *M. hominis* and *U. urealyticum*, respectively. Species verification was also accomplished on the basis of colony characteristics on Mycotrim GU medium, Dienes staining and biochemical reactions.

Library construction and screening of clones

A library was constructed using genomic DNA isolated from *M. hominis* ATCC 23114 by the method of Razin et al. (1983) *Int. J. Sys. Bacteriol.* 33:201–206. Digestion of this DNA with EcoRI was performed according to the manufacturer's instructions (GibcoBRL, Bethesda, Md.). Restriction fragments were ligated into EcoRI-hydrolyzed pUCl18 using T4 DNA ligase as described by Sugino et al. (1977) *J. Biol. Chem.* 252:3987–3994. Competent *E. coli* DH5α cells were transformed using the procedure of Hanahan [(1983) *J. Mol. Biol.* 166:577–580] and then grown on Luria-Bertani (LB) agar containing 50 µg/ml ampicillin. The presence of *M. hominis* DNA caused insertional inactivation of the β-galactosidase gene and such bacterial colonies appeared white when grown on X-gal and IPTG according to established procedures (Sambrook et al. 1989). Recombinant plasmids were isolated by a miniprep boiling lysis method [Holmes et al. (1981) *Anal. Biochem.* 114:193–197]. Plasmid DNA was digested with EcoRI and other restriction enzymes, then electrophoresed on standard 1% (w/v) agarose gels containing 1 µg/ml of ethidium bromide. DNA was visualized by UV fluorescence. The *M. hominis* insert DNA was sized by comparison with a standard 1 Kb ladder of DNA markers (GibcoBRL).

Selection of *M. hominis*-specific probe

DNA inserts liberated from recombinant plasmids were blotted onto nylon filters (Boehringer-Mannhiem Biochemicals) by Southern transfer [Southern (1975) *J. Mol. Biol.* 98.:503–517). These immobilized inserts were tested for hybridization with *Ureaplasma urealyticum* chromosomal DNA which had been digested with DraI and labeled with digoxigenin-UTP (DIG-UTP) using a Geneus® kit from Boehringer-Mannhiem Biochemicals. Inserts which hybridized with *U. urealyticum* chromosomal DNA were detected with alkaline phosphatase-conjugated anti-digoxigenin antibody and visuallized with the chemiluminescent substrate Lumi-Phos 530®, according to methods outlined for the Geneus® System (Boehringer-Mannhiem Biochemicals). Any clone which hybridized with *U. urealyticum* chromosomal DNA was eliminated as not being *M. hominis*-specific. Clones containing inserts which did not hybridize with *U. urealyticum* genomic DNA were initially presumed to contain *M. hominis*-specific DNA.

*M. hominis* specificity was verified by labeling clone inserts for use as hybridization probes on Southern blots and dot blots of PstI- or EcORI-digested genomic DNA from various Mycoplasma species, including *U. urealyticum, M. orale, M. genitalium, M. pneumoniae, M. salivarium* and *M. hyorhinis*.

Dot blots were made by incubating one volume of purified Mycoplasma DNA with nine volumes of denaturing solution (4M NaOH, 100 mM EDTA) at room temperature for 10 min. One microliter of DNA sample was spotted onto a dry Boehringer Mannheim positively-charged nylon membrane. The DNA was fixed onto the memebrane by UV crosslinking for 10 min.

Clones containing recombinant plasmids which hybridized only with restriction fragments from *M. hominis* genomic DNA were selected as *M. hominis*-specific probes. DNA sequencing The selected *M. hominis*-specific inserts were isolated from pUCl18 by excision with EcoRI followed by electrophoresis in a 1% agarose gel. DNA was extracted from the gel using GENECLEAN® (Bio 101, La Jolla, Calif.) and hydrolyzed with HindIII. EcoRI/HindIII subfragments were ligated into M13mp18 and M13mp19, and the resulting ligation mix transformed into *E. coli* DH5αF' cells. Colonies containing recombinant plasmids were selected by growth on LB agar containing 60 μg/ml ampicillin in the presence of X-gal (5-bromo-4-chloro-3-indolyl-β-D-galactoside) and IPTG (isopropyl-β-D-thiogalactopyranoside). Plasmids were isolated from white colonies and nucleotide sequences were determined by the dideoxy chain termination method of Sanger et al. (1977 Proc. Natl. Acad. Sci. USA 74:5463–5467) using a Sequenase® Kit (United States Biochemical Corporation, Cleveland, Ohio). Sequence comparisons were performed using the programs of the Genetics Computer Group (University of Wisconsin, Madison, Wis.).

EXAMPLE 2

MYCOPLASMA HOMINIS-SPECIFIC PROBES

Several clones were obtained from an *M. hominis* genomic library which hybridized with total genomic DNA of *M. hominis* but not that of *U. urealyticum*. One clone in particular contained a plasmid designated pMhom-120 which hybridized with PstI- or EcoRI-hydrolyzed *M. hominis* DNA but not with similarly hydrolyzed DNA from other Mycoplasma species (FIG. 2).

Figure 2B:
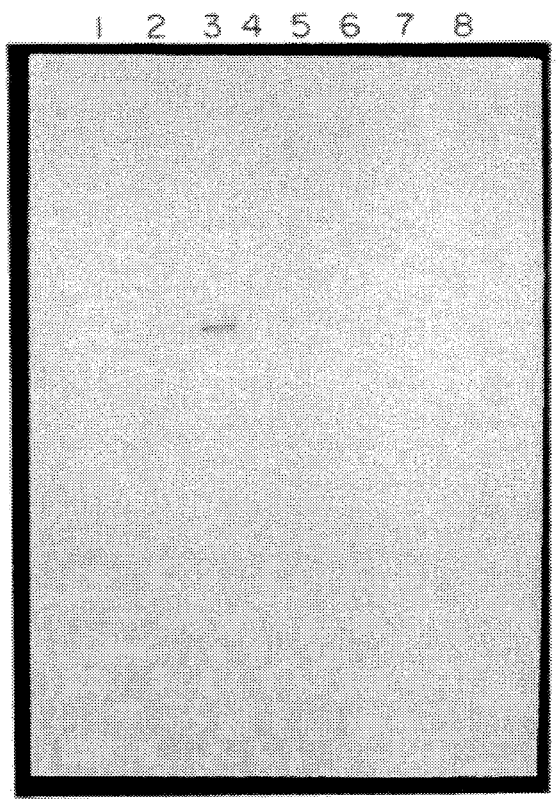

FIG. 2A depicts an ethidium bromide-stained 1% agarose gel containing electrophoretically-separated, EcoRI-digested genomic DNA from *M. genitalium, M. hominis, M. hyorhinis, M. orale, M. pneumoniae, M. salivarium* and *M. urealyticum* (lanes 2–8, respectively). Lane 1 contained molecular weight markers (a 1 kb ladder®, GIBCO-Brl). FIG. 2B depicts an autoradiogram of a Southern blot made from the gel depicted in FIG. 2A which had been hybridized with a labeled pMhom120 probe. As illustrated, the pMhom120 probe hybridized only with a single 2000 bp fragment of *M. hominis* genomic DNA.

pMhom-120 contained an insert of about 2000 bp which, when digested with HindIII, yielded two HindIII inserts having approximate sizes of 500 and 1500 bp. The 500 bp HindIII restriction fragment was subcloned into pUCl18 to produce pMh5 and further analyzed for *M. hominis*-specificity by dot blot hybridization as described in Example 1.

Figure 3:
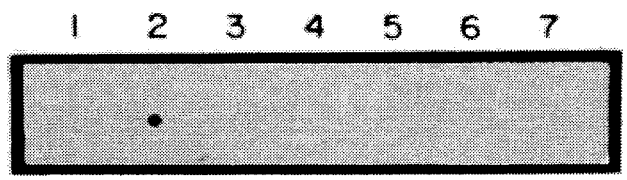

DNA in pMh5 is highly specific for *M. hominis* genomic DNA. As depicted in FIG. 3, a probe made from the pMh5 insert hybridized only with *M. hominis* genomic DNA and not with DNA from closely related Mycoplasma species *M. genitalium, M. hominis, M. hyorhinis, M. orale, M. pneumoniae, M. salivarium* or *U. urealyticum*.
Sequencing and Analysis of the pMh5

Sequencing of the pMh5 insert was accomplished by the dideoxy chain termination method as described in Example 1.

Sequencing revealed that the pMh5 was 471 bp; this 471 bp pMh5 insert is provided as SEQ ID NO:1. A 152 bp portion (positions 105–256) of SEQ ID NO:1 was selected as a possible target for PCR amplification, e.g. when using oligonucleotides having SEQ ID NO:5 and 6. This sequence of this 152 bp fragment is provided as SEQ ID NO:3. No significant homologies were found when this sequence or the oligonucleotide primers (SEQ ID NOS:4–7) were tested using the gene sequence analysis program of the Genetics Computer Group (GCG, University of Wisconsin, Madison Wis.).

EXAMPLE 3

PCR AMPLIFICATION OF *M. HOMINIS*-SPECIFIC DNA

Selection of oligonucleotide primers

The oligonucleotide primers which could specifically generate an *M. hominis*-specific DNA each had 20 deoxyribonucleotides. Four oligonucleotide primers, named Mh1, Mh2, Mh3 and Mh4, were selected as having particular utility for generating an *M. hominis*-specific DNA. The sequences of these primers were:

Mh1: 5'-CTACAATGGTTGTTGCCCTC-3' (SEQ ID NO:4);

Mh2: 5'-GGTGATTCACGCTTGTATGC-3' (SEQ ID NO:5);

Mh3: 5'-GGTCCTAGACAACTTATAAG-3' (SEQ ID NO:6); and

Mh4: 5'-ATCGTGTAATCCATCGGATG-3' (SEQ ID NO:7).

Mh1 corresponds to positions 52–71 of SEQ ID NO:1; Mh2 corresponds to positions 105–124 of SEQ ID NO:1; Mh3 corresponds to positions 262–243 of SEQ ID NO:1; and Mh4 corresponds to positions 350–331 of SEQ ID NO:1.

The suitability of these primers for specific PCR amplification of the target sequence and the determination of their individual properties were accomplished using the OLIGO software system (National Bioscience, Hamel, Minn.). Primers were synthesized by Midland Certified Reagent Company (Midland, Tex.).
PCR Amplification PCR amplification was performed using a Techne PHC-3 Dri-Block Cycler® (Techne Corp., Princeton, N.J.) and a GeneAmp® PCR reagent kit with AmpliTaq® DNA polymerase (Perkin Elmer Cetus, Norwalk, Conn.).

The temperature and duration of each step in the PCR amplification cycle was determined from the melting temperatures of the primers.

DNA was extracted from mycoplasmacae contained in pure cultures or from clinical specimens of body fluids. Mycoplasma species tested include *U. urealyticum, M. hominis, M. orale, M. genitalium, M. pneumoniae, M. salivarium* and *M. hyorhinis*. A 1 ml culture or specimen sample was centrifuged in a microcentrifuge at 1400 x g for 15 min in a microcentrifuge. The precipitate was resuspended in 100 μl of distilled water, boiled for 10 min and stored at 20° C. until analysis. DNA obtained from pure *M. hominis* cultures served as a positive control in all PCR analyses.

DNA for PCR analysis was also extracted from cotton swabs used to collect clinical specimens. Each cotton swab was placed in a tube containing 1 ml sterile distilled water and vortexed gently for 15 seconds. The swab was discarded and the tube was centrifuged to remove cellular debris. Supernatants were placed in microfuge tubes, boiled for 10 min and stored at 20° C. until analysis.

Prior to DNA synthesis by PCR, the frozen pellets were resuspended in 50 µl of sterile distilled water, boiled for 10 minutes, and then immediately placed on ice. Twenty-five B1 of DNA sample was added to 75 µl of PCR mix to provide a mixture containing 50 mM Tris (pH 8.3), 1.5 mM $MgCl_2$, 200 mM of each deoxyribonucleotide, 0.25 U of Taq polymerase and 0.15 mM of each primer. An overlay of 50 µl mineral oil was added to each tube. PCR was conducted in sterile, disposable tubes to prevent cross contamination.

After an initial denaturation step of 95° C. for 3 min, 35 cycles of PCR amplification were performed. Each cycle consisted of denaturation at 94° C. for 1 min, primer annealing at 60° C. for 1 min, and primer extension at 72° C. for 1 min. The final cycle included a 5 min primer extension step to insure that all synthesized DNA fragments were completely extended.

After amplification the mineral oil was removed from the aqueous PCR reagent mixture and 25 µl of the mixture was electrophoresed for 30 min in a 2% (w/v) NuSieve GTG agarose gel (FMC, Rockland, Me.) prepared with Tris-Acetate-EDTA (40 mM Tris, 20 mM Acetic Acid, 1 mM EDTA) containing 0.5 µg/ml of ethidium bromide. A 1 kb DNA Ladder, a 100 bp DNA Ladder (GIBCOBRL) or a BioMarker Low Ladder (BioVentures, Murfreesboro, Tenn.) were used as size standards on gels. Linear regression analysis verified the size of the synthesized DNA fragment.

Figure 4A:
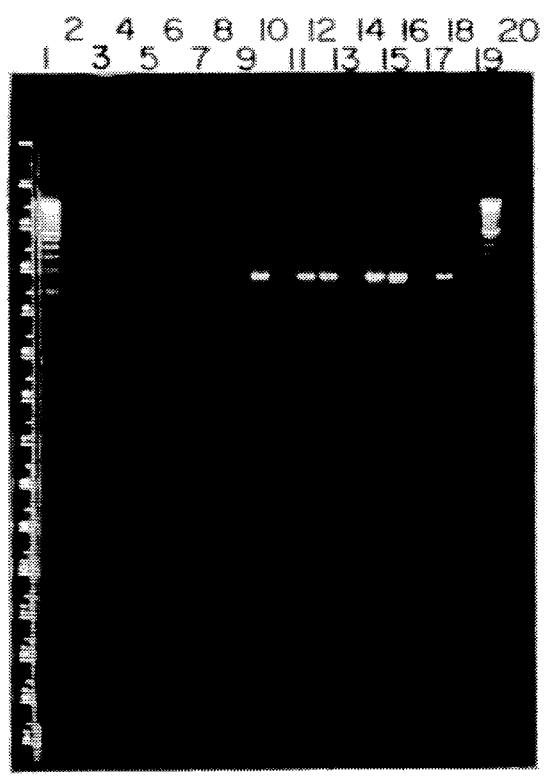
Figure 4B:
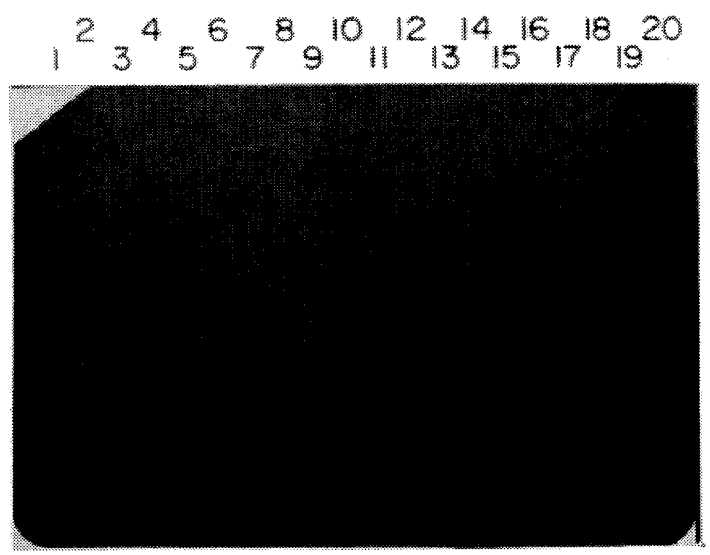

As depicted in FIG. 4, the selected PCR conditions and oligonucleotides having SEQ ID NOS: 5 and 6 resulted in synthesis of an *M. hominis* DNA fragment from clinical samples derived from different sources and from *M. hominis* positive controls (lane 3), but did not result in synthesis of DNA from samples containing different Mycoplasma species. The size of this band was about 150 bp, corresponding to the size of a DNA fragment having SEQ ID NO:3. This detection assay for *M. hominis* was performed in less than six hours.

Figure 5:

FIG. 5 illustrates the sensitivity of this PCR procedure. In particular, FIG. 5 depicts an agarose gel containing the PCR amplified product generated using decreasing amounts of *M. hominis* genomic DNA and oligonucleotides having SEQ ID NOS: 5 and 6. Lanes 2–7 contain the PCR product generated from 100 femtograms (fg), 10 fg, 1 fg, 100 attograms (ag), 10 ag and 1 ag, respectively. Lane 1 contains a 100 bp ladder of molecular weight markers. A single band which migrated between the 100 and 200 bp markers was produced; this band contains a 152 bp DNA fragment having SEQ ID NO:3.

As illustrated the PCR procedure described above can detect as little as 10 fg ($10 \times 10^{-15}$ g) of *M. hominis* genomic DNA. This amount of *M. hominis* genomic DNA contains only about 18 molecules of target DNA. These data indicate that as little as 18 *M. hominis* bacteria can be detected using the present PCR amplification method.

EXAMPLE 4

IN SITU HYBRIDIZATION TO MYCOPLASMA HOMINIS RNA

Preparation of Probes

*M. hominis*-specific nucleic acids and oligonucleotides, e.g. having SEQ ID NOS: 1 and 3–7(FIG. 1), are radioactively labeled with $^3$H or $^{35}$S by standard procedures (Sambrook et al. 1989). For example, *M. hominis*-specific RNA probes can be made by transcription from an *M. hominis* template using SP6, T3 or T7 RNA polymerase as described in Serook et al.

In Situ Hybridization of Oligonucleotide Probes

Cells in clinical samples are harvested at 14,000 × g for 15 min to produce a visible cellular pellet. The pellet is resuspended in 50 µl of PBS (5.7M NaCl, 100 mM sodium phosphate, pH 7.5) and 5 µl of 37% formaldehyde is added. The cell suspension is spread on a poly-L-lysine coated slide and the cell smears are air dried at room temperature. The slides are either stored at −20° C. or processed immediately.

Slides are fixed in 3.7% formaldehyde and 90% methanol for 10 min at room temperature, washed briefly in distilled water, and placed in 100 mM Tris-HCl, pH 8.0, 50 mM Na borohydrate for 30 min in the dark with rapid stirring. The slides are then briefly rinsed with distilled water.

Slides are placed in hybridization solution (5X SET: 750 mM NaCl, 100 mM Tris-HCl, pH 7.8 and 5 mM EDTA; 0.1% SDS can be added to reduce background) for 1–20 hr. Hybridization is conducted with about 30 µl of 5X SET containing 50 ng of oligonucleotide probe (i.e., about 1.7 ng oligonucleotide/µl SET). After the hybridization solution is applied, a cover slip is placed on the slide and slides are incubated in a humid chamber at room temperature overnight.

Cover slips are removed by immersing the slide in 5X SET. The slides are washed 3 times for 10 min in 0.2X SET at 37° C.

The presence of *M. hominis* infection is detected, for example, by dipping slides in photoemulsion solution (Kodak) and observing silver grains which were formed by exposure of the emulsion to $^3$H or $^{35}$S radioactivity using a microscope.

Evans Blue (2% aqueous solution) or Giemsa can used as a counterstain. Slides are air dried before mounting with SAVA mounting fluid.

---

What is claimed is:

1. A method of detecting Mycoplasma hominis comprising:
   a) amplifying a *Mycoplasma hominis* target nucleic acid by contacting a sample to be tested for the presence of *Mycoplasma hominis* with at least one oligonucleotide for a time and under conditions sufficient to produce copies of said target nucleic acid, wherein said oligonucleotide consists of at least 14 contiguous nucleotides of Mycoplasma hominis DNA of pMhom120 having ATCC Accession Number 97512, or wherein said oligonucleotide has at least about 70% complementarity to at least 14 contiguous nucleotides of SEQ ID NO:1 or SEQ ID NO:3, such that said complementarity is sufficient to permit said amplification, and wherein said oligonucleotide does not hybridize to genomic DNA of *Ureaplasma urealyticum, Mycoplasma genitalium, Mycoplasma hyorhinis, Mycoplasma orale, Mycoplasma pneumoniae* or *Mycoplasma salivarium;* and
   b) detecting said nucleic acid copies, thereby detecting Mycoplasma hominis.

2. A method of detecting *Mycoplasma hominis* comprising:
   a) contacting a *Mycoplasma hominis* target nucleic acid in a sample to be tested for the presence of *Mycoplasma hominis* with at least one oligonucleotide probe for a time and under conditions to permit hybridization between said oligonucleotide probe and said nucleic acid target, wherein said oligonucleotide probe consists of at least 14 contiguous nucleotides of *Mycoplasma hominis* DNA of pMhom120 having ATCC Accession Number 97512, or wherein said probe has at least about 70% complementarity to at least 14 contiguous nucleotides of SEQ ID NO:1 or SEQ ID NO:3, such that said probe is sufficiently complementary to hybridize to said target nucleic acid, and wherein said oligonucleotide probe does not hybridize to genomic DNA of *Ureaplasma urealyticum, Mycoplasma genitalium, Mycoplasma hyorhinis, Mycoplasma orale, Mycoplasma pneumoniae* or *Mycoplasma salivarium;* and
   b) detecting said hybridization thereby detecting said *Mycoplasma hominis.*

3. A method of detecting Mycoplasma hominis comprising:
   a) amplifying a *Mycoplasma hominis* target nucleic acid by contacting a sample to be tested for the presence of *Mycoplasma hominis* with at least one oligonucleotide for a time and under conditions sufficient to produce copies of said target nucleic acid, wherein said oligonucleotide consists of at least 14 contiguous nucleotides of SEQ ID NO:1, SEQ ID NO:3, SEQ ID NO:4, SEQ ID NO:5, SEQ ID NO:6 or SEQ ID NO:7, or wherein said oligonucleotide has at least about 70% complementarity to at least 14 contiguous nucleotides of SEQ ID NO:1, SEQ ID NO:3, SEQ ID NO:4, SEQ ID NO:5, SEQ ID NO:6 or SEQ ID NO:7, such that said complementarity is sufficient to permit said amplification, and wherein said oligonucleotide does not hybridize to genomic DNA of *Ureaplasma urealyticum, Mycoplasma genitalium, Mycoplasma hyorhinis, Mycoplasma orale, Mycoplasma pneumoniae* or *Mycoplasma salivarium;* and
   b) detecting said nucleic acid copies, thereby detecting said *Mycoplasma hominis.*

4. A method of detecting *Mycoplasma hominis* comprising:
   a) contacting a *Mycoplasma hominis* target nucleic acid in a sample to be tested for the presence of *Mycoplasma hominis* with at least one oligonucleotide probe for a time and under conditions to permit hybridization between said oligonucleotide probe and said nucleic acid target, wherein said oligonucleotide probe consists of at least 14 contiguous nucleotides of SEQ ID NO:1, SEQ ID NO:3, SEQ ID NO:4, SEQ ID NO:5, SEQ ID NO:6 or SEQ ID NO:7, or wherein said probe has at least about 70% complementarity to at least 14 contiguous nucleotides of SEQ ID NO:1, SEQ ID NO:2, SEQ ID NO:3, SEQ ID NO:4, SEQ ID NO:5, SEQ ID NO:6 or SEQ ID NO:7, such that said probe is sufficiently complementary to hybridize to said target nucleic acid, and wherein said oligonucleotide does not hybridize to genomic DNA of *Ureaplasma urealyticum, Mycoplasma genitalium, Mycoplasma hyorhinis, Mycoplasma orale, Mycoplasma pneumoniae* or *Mycoplasma salivarium;* and
   b) detecting said nucleic acid copies, thereby detecting said *Mycoplasma hominis.*

5. An isolated nucleic acid consisting of at least 14 contiguous nucleotides of *Mycoplasma hominis* DNA of pMhom120 having ATCC Accession Number 97512, or having at least about 70% complementarity to at least 14 contiguous nucleotides of SEQ ID NO:1 or SEQ ID NO:3, and wherein said oligonucleotide does not hybridize to genomic DNA of *Ureaplasma urealyticum, Mycoplasma genitalium, Mycoplasma hyorhinis, Mycoplasma orale, Mycoplasma pneumoniae* or *Mycoplasma salivarium.*

6. An isolated nucleic acid consisting of at least 14 contiguous nucleotides of SEQ ID NO:1, SEQ ID NO:3, SEQ ID NO:4, SEQ ID NO:5, SEQ ID NO:6 or SEQ ID NO:7, or having at least about 70% complementarity to at least 14 contiguous nucleotides of SEQ ID NO:1, SEQ ID NO:3, SEQ ID NO:4, SEQ ID NO:5, SEQ ID NO:6 or SEQ ID NO:7, and wherein said oligonucleotide does not hybridize to genomic DNA of *Ureaplasma urealyticum, Mycoplasma genitalium, Mycoplasma hyorhinis, Mycoplasma orale, Mycoplasma pneumoniae* or *Mycoplasma salivarium.*

7. The method of any one of claims 1, 2, 3, or 4, wherein said *Mycoplasma hominis* target nucleic acid comprises the approximately 2000 bp *Mycoplasm hominis* nucleic acid insert of plasmid pMhom120 having ATCC Accession Number 97512.

8. The method of any one of claims 1, 2, 3, or 4 wherein said *Mycoplasma hominis* target nucleic acid comprises the approximately 471 bp *Mycoplasma hominis* nucleic acid insert of plasmid pMh5 having ATCC Accession Number 97512.

9. The method of any one of claims 1, 2, 3, or 4 wherein said *Mycoplasma hominis* target nucleic acid comprises SEQ ID NO:1.

10. The method of any one of claims 1, 2, 3, or 4 wherein said *Mycoplasma hominis* target nucleic acid comprises SEQ ID NO:3.

11. The method of any one of claims 1, 2, 3, or 4 wherein said *Mycoplasma hominis* target nucleic acid comprises a nucleotide sequence complementary to SEQ ID NO:4.

12. The method of any one of claims 1, 2, 3, or 4 wherein said *Mycoplasma hominis* target nucleic acid comprises a nucleotide sequence complementary to SEQ ID NO:5.

13. The method of any one of claims 1, 2, 3, or 4 wherein said *Mycoplasma hominis* target nucleic acid comprises a nucleotide sequence complementary to SEQ ID NO:6.

14. The method of any one of claims 1, 2, 3, or 4 wherein said *Mycoplasma hominis* target nucleic acid comprises a nucleotide sequence complementary to SEQ ID NO:7.

15. The method of claim 1 or 3 wherein said oligonucleotide has the sequence depicted in SEQ ID NO:4.

16. The method of claim 1 or 3 wherein said oligonucleotide has the sequence depicted in SEQ ID NO:5.

17. The method of claim 1 or 3 wherein said oligonucleotide has the sequence depicted in SEQ ID NO:6.

18. The method of claim 1 or 3 wherein said oligonucleotide has the sequence depicted in SEQ ID NO: 7.

19. The method of claim 1, 2, 3, or 4 which comprises contacting said sample with two oligonucleotides.

20. The method of claim 19 wherein one oligonucleotide has SEQ ID NO:5 and the other oligonucleotide has SEQ ID NO:6.

21. The method of claim 19 wherein one oligonucleotide has SEQ ID NO:4 and the other oligonucleotide has SEQ ID NO:7.

22. The method of claim 2 or 4 wherein said probe has the sequence depicted in SEQ ID NO:4.

23. The method of claim 2 or 4 wherein said probe has the sequence depicted in SEQ ID NO: 5.

24. The method of claim 2 or 4 wherein said probe has the sequence depicted in SEQ ID NO:6.

25. The method of claim 2 or 4 wherein said probe has the sequence depicted in SEQ ID NO:7.

26. The method of claim 1 or 2 wherein said oligonucleotide is at least about 70% complementary to SEQ ID NO:1.

27. The method of claim 1 or 2 wherein said oligonucleotide is at least about 80% complementary to SEQ ID NO:1.

28. The method of claim 1 or 2 wherein said oligonucleotide is at least about 90% complementary to SEQ ID NO: 1.

29. The method of claim 1 or 2 wherein said probe is at least about 70% complementary to SEQ ID NO:3.

30. The method of claim 1 or 2 wherein said probe is at least about 80% complementary to SEQ ID NO:3.

31. The method of claim 1 or 2 wherein said probe is at least about 90% complementary to SEQ ID NO:3.

32. The method of claim 1 or 3 wherein said method further comprises contacting said target nucleic acid with ATP, CTP, GTP, UTP, dATP, dCTP, dGTP or dTTP.

33. The method of claim 1 or 2 wherein said method further comprises contacting said target nucleic acid with salt, cation or pH conditions sufficient to permit amplification of said target nucleic acid by said amplification enzyme.

34. The method of claim 1 or 3 wherein said target nucleic acid is double-stranded.

35. The method of claim 34 wherein said method further comprises denaturing said target nucleic acid.

36. The method of claim 35 wherein said method further comprises cooling said target nucleic acid to a temperature at which said oligonucleotide hybridizes to said target nucleic acid.

37. The method of claim 36 wherein said method further comprises incubating said target nucleic acid with said oligonucleotide at a temperature at which the amplification enzyme produces copies of said target nucleic acid.

38. The method of claim 1 or 3 wherein said target nucleic acid is single-stranded.

39. The method of claim 38 wherein said target nucleic acid is RNA.

40. The method of claim 39 which further comprises making a cDNA copy of said RNA.

41. The method of claim 40 wherein said cDNA copy is made by reverse transcriptase.

42. The method of claim 40 which further comprises producing a copy of said cDNA copy.

43. The method of claim 42 wherein said copy is made by an RNA polymerase or a Qβ replicase.

44. The method of claim 1 or 3 wherein said oligonucleotide further comprises a recognition sequence for the binding of said amplification enzyme.

45. The method of claim 44 wherein said recognition sequence is an RNA polymerase binding site or a Qβ replicase binding site.

46. The method of claim 1 or 3 wherein said method is a polymerase chain reaction, transcription-based amplification, self-sustained sequence replication, ligase-based amplification, Qβ-replicase RNA replication or run-off transcription.

47. The method of claim 1 or 3 wherein said amplification enzyme is *Escherichia coli* DNA polymerase I, Klenow fragment of *E. coli* DNA polymerase I, T4 DNA polymerase, T7 DNA polymerase, *Thermus aquaticus* DNA polymerase, *Thermococcus litoralis* DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Qβ replicase.

48. The method of any one of claims 1, 2, 3, or 4 wherein said sample is an animal body fluid, an animal secretion, an animal tissue, a culture medium or a transport medium.

49. The method of claim 2 or 4 wherein a reporter molecule is attached to said probe.

50. The method of claim 49 wherein said reporter molecule is a fluorophore, bioluminescent molecule, chemiluminescent molecule, biotin, digoxigenin, avidin, streptavidin, enzyme or radioisotope.

51. The method of claim 2 or 3 wherein said hybridization is solid-phase-based hybridization, solution hybridization or in situ hybridization.

52. The method of claim 51 wherein said solid phase is a filter or a bead.

53. An isolated *Mycoplasma hominis* nucleic acid having SEQ ID NO:1.

54. An isolated *Mycoplasma hominis* nucleic acid having SEQ ID NO:3.

55. An isolated *Mycoplasma hominis* nucleic acid having SEQ ID NO:4.

56. An isolated *Mycoplasma hominis* nucleic acid having SEQ ID NO:5.

57. An isolated *Mycoplasma hominis* nucleic acid having SEQ ID NO:6.

58. An isolated *Mycoplasma hominis* nucleic acid having SEQ ID NO:7.

59. An isolated nucleic acid having the approximately 2000 bp *Mycoplasma hominis* DNA insert of recombinant plasmid pMhom120 having ATCC Accession Number 97512.

60. An isolated nucleic acid having an antisense nucleotide sequence of SEQ ID NO:1 wherein said nucleic acid is fully complementary to SEQ ID NO: 1.

61. An isolated nucleic acid consisting of plasmid pMhom120 having ATCC Accession Number 97512.

62. A compartmentalized kit for detection of *Mycoplasma hominis* comprising a first receptacle containing at least one of the nucleic acids of any one of claims 5, 6 and 53–59.

63. The kit of claim 62 which further comprises a receptacle containing at least one isolated *Ureaplasma urealyticum* nucleic acid probe for detection of *Ureaplasma urealyticum* wherein said nucleic acid probe has any one of the sequences of SEQ ID NOS: 8–16.

64. The kit of claim 63 which further comprises a receptacle containing an *Mycoplasma hominis* nucleic acid standard for use as a positive control.

65. The kit of claim 64 wherein said *Mycoplasma hominis* nucleic acid standard is *Mycoplasma hominis* genomic DNA, plasmid pMhom120 or plasmid pMh5.

66. The kit of claim 64 wherein said *Mycoplasma hominis* nucleic acid standard is an isolated DNA having SEQ ID NO:1 or SEQ ID NO:3.

67. The kit of claim 63 which further comprises a receptacle containing a reagent for in vitro nucleic acid amplification.

68. The kit of claim 67 wherein said reagent is an amplification enzyme.

69. The kit of claim 68 wherein said amplification enzyme is *Escherichia coli* DNA polymerase I, Klenow fragment of *Escherichia coli* DNA polymerase I, T4 DNA polymerase, T7 DNA polymerase, *Thermus aquaticus* DNA polymerase, *Thermococcus litoralis* DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *Escherichia coli* DNA ligase or Qβ replicase.

70. The kit of claim 63 wherein said nucleic acid is linked to a reporter molecule.

71. The kit of claim 70 wherein said reporter molecule is a fluorophore, a bioluminescent molecule, a chemiluminescent molecule, a radioisotope, biotin, digoxigenin, avidin, streptavidin or an enzyme.

72. The kit of claim 70 wherein said reporter molecule is digoxigenin.

73. The kit of claim 72 which further comprises an anti-digoxigenin antibody for detecting said digoxigenin.

74. A recombinant expression vector having the nucleic acid of any one of claims 5, 6 and 53–59 operably linked to segment of said vector which can effect expression of said nucleic acid.

75. A host cell having the nucleic acid of any one of claims 5, 6 and 53–59.

76. A host cell having the expression vector of claim 74.

* * * * *

UNITED STATES PATENT AND TRADEMARK OFFICE
CERTIFICATE OF CORRECTION

PATENT NO. : 5,595,871
DATED : January 21, 1997
INVENTOR(S) : Vito G. DelVecchio, et al.

It is certified that error appears in the above-identified patent and that said Letters Patent is hereby corrected as shown below:

Column 1, line 7: "F49620-85-C001 and F49620-88-C0053" should read "F49620-85-C-0013, F49620-88-C0053 and F33615-90-C-0606 --
Column 12, line 40: "about about" should read --about--
Column 13, line 48: "havaing" should read --having--
Column 15, line 8: "No" should read --NO--
Column 20, line 5: "embodiement" should read --embodiment--
Column 20, line 40: "Labortory" should read --Laboratory--
Column 22, line 39: "prcedures" should read --procedures--
Column 22, line 51: "rasied" should read --raised--
Column 23, line 2: "cognozant" should read --cognizant--
Column 25, line 65: "≅" should read -- - --
Column 26, line 54: "visuallized" should read --visualized--
Column 27, line 46: "M"(fourth occurrence) should read --U--.
Column 29, line 11: "Bl" should read --µl--
Column 40, line 43, Claim 7: "Mycoplasm" should read --Mycoplasma--

Signed and Sealed this

Twenty-seventh Day of April, 1999

Attest:

Q. TODD DICKINSON

*Attesting Officer*   *Acting Commissioner of Patents and Trademarks*

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 471 base pairs (B) TYPE: nucleic acid
(C) STRANDEDNESS: both
(D) TOPOLOGY: linear (ii) MOLECULE TYPE: DNA (genomic)

(ix) FEATURE:
 (A) NAME/KEY: CDS
 (B) LOCATION: 3..470

(xi) SEQUENCE DESCRIPTION: SEQ ID NO:1:

```
AA GCT TTA GTT AAT TAT GCA AAA GAG TAT ACT GAA TTT GAA GAT ATG        47
   Ala Leu Val Asn Tyr Ala Lys Glu Tyr Thr Glu Phe Glu Asp Met
   1               5                   10                  15

GGG ACT ACA ATG GTT GTT GCC CTC ATT TTT AAT GCA AAT GGT TTA GCT        95
Gly Thr Thr Met Val Val Ala Leu Ile Phe Asn Ala Asn Gly Leu Ala
                    20                  25                  30

TAT GTC TTT AAT ATT GGT GAT TCA CGC TTG TAT GCA TAC AAT GGA TTA       143
Tyr Val Phe Asn Ile Gly Asp Ser Arg Leu Tyr Ala Tyr Asn Gly Leu
                35                  40                  45

CTT TAT CAA ATC ACA GAA GAT CAA AAT TAT TTA TAT CAG TTA ATG AGA       191
Leu Tyr Gln Ile Thr Glu Asp Gln Asn Tyr Leu Tyr Gln Leu Met Arg
            50                  55                  60

GAA TTT AAT TTA ACA TAC GAA GAA GCA GCA TTA GAT CCT AAT TCA TAC       239
Glu Phe Asn Leu Thr Tyr Glu Glu Ala Ala Leu Asp Pro Asn Ser Tyr
        65                  70                  75

AAA CTT ATA AGT TGT CTA GGA CCA AAT AAA AAA ACC AAT TGT CAA TCA       287
Lys Leu Ile Ser Cys Leu Gly Pro Asn Lys Lys Thr Asn Cys Gln Ser
80                  85                  90                  95

TTT TTT ATA TCA CAA AAA TCA GCA GTT AAA TAT TAT TTA TTA ACA TCC       335
Phe Phe Ile Ser Gln Lys Ser Ala Val Lys Tyr Tyr Leu Leu Thr Ser
                    100                 105                 110

GAT GGA TTA CAC GAT TAT GTT TCT AAA CCA ATA ATA GAA ACT GTT TTG       383
Asp Gly Leu His Asp Tyr Val Ser Lys Pro Ile Ile Glu Thr Val Leu
                115                 120                 125

CAA ACA AAT AAG AGT TTA AAA GAT AAG TTA AAC CTT CTA ATA AAA TAT       431
Gln Thr Asn Lys Ser Leu Lys Asp Lys Leu Asn Leu Leu Ile Lys Tyr
            130                 135                 140

GCC AAA AAA AAT CTT TCA AAA GAC AAT ATA ACC GGA ATT C                 471
Ala Lys Lys Asn Leu Ser Lys Asp Asn Ile Thr Gly Ile
            145                 150                 155
```

(2) INFORMATION FOR SEQ ID NO:2:

(i) SEQUENCE CHARACTERISTICS:
 (A) LENGTH: 156 amino acids
 (B) TYPE: amino acid
 (D) TOPOLOGY: linear (ii) MOLECULE TYPE: protein (xi) SEQUENCE DESCRIPTION: SEQ ID NO:2:

```
Ala Leu Val Asn Tyr Ala Lys Glu Tyr Thr Glu Phe Glu Asp Met Gly
1               5                   10                  15

Thr Thr Met Val Val Ala Leu Ile Phe Asn Ala Asn Gly Leu Ala Tyr
                20                  25                  30

Val Phe Asn Ile Gly Asp Ser Arg Leu Tyr Ala Tyr Asn Gly Leu Leu
            35                  40                  45

Tyr Gln Ile Thr Glu Asp Gln Asn Tyr Leu Tyr Gln Leu Met Arg Glu
        50                  55                  60

Phe Asn Leu Thr Tyr Glu Glu Ala Ala Leu Asp Pro Asn Ser Tyr Lys
65                  70                  75                  80

Leu Ile Ser Cys Leu Gly Pro Asn Lys Lys Thr Asn Cys Gln Ser Phe
```

|     |     |     |     |     | 85  |     |     |     |     | 90  |     |     |     |     | 95  |     |     |
| --- | --- | --- | --- | --- | --- | --- | --- | --- | --- | --- | --- | --- | --- | --- | --- | --- | --- |
| Phe | Ile | Ser | Gln | Lys | Ser | Ala | Val | Lys | Tyr | Tyr | Leu | Leu | Thr | Ser | Asp |     |     |
|     |     |     |     | 100 |     |     |     |     | 105 |     |     |     |     | 110 |     |     |     |
| Gly | Leu | His | Asp | Tyr | Val | Ser | Lys | Pro | Ile | Ile | Glu | Thr | Val | Leu | Gln |     |     |
|     |     |     | 115 |     |     |     |     | 120 |     |     |     |     | 125 |     |     |     |     |
| Thr | Asn | Lys | Ser | Leu | Lys | Asp | Lys | Leu | Asn | Leu | Leu | Ile | Lys | Tyr | Ala |     |     |
|     | 130 |     |     |     |     | 135 |     |     |     |     | 140 |     |     |     |     |     |     |
| Lys | Lys | Asn | Leu | Ser | Lys | Asp | Asn | Ile | Thr | Gly | Ile |     |     |     |     |     |     |
| 145 |     |     |     |     | 150 |     |     |     |     |     | 155 |     |     |     |     |     |     |

( 2 ) INFORMATION FOR SEQ ID NO:3:

( i ) SEQUENCE CHARACTERISTICS:
        ( A ) LENGTH: 152 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:3:

```
GGTGATTCAC GCTTGTATGC ATACAATGGA TTACTTTATC AAATCACAGA AGATCAAAAT         60
TATTTATATC AGTTAATGAG AGAATTTAAT TTAACATACG AAGAAGCAGC ATTAGATCCT        120
AATTCATACA AACTTATAAG TTGTCTAGGA CC                                     152
```

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
CTACAATGGT TGTTGCCCTC                                                    20
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
GGTGATTCAC GCTTGTATGC                                                    20
```

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
GGTCCTAGAC AACTTATAAG                                                    20
```

( 2 ) INFORMATION FOR SEQ ID NO:7:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

ATCGTGTAAT CCATCGGATG                                                         20

( 2 ) INFORMATION FOR SEQ ID NO:8:

( i ) SEQUENCE CHARACTERISTICS:
        ( A ) LENGTH: 290 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:8:

ATCTGATGAA ACTAAATTTA TTGTTGTTAA AGTTTTAGAT ATTGGTGATG AAAAACAACA             60
AATGGTTGTT TATGATGAAT TACGAATTTC AAATTTAATT AAGAATTCAA ACTCTGATAA            120
AAGAAGTTAT ATCATGGAAT ATTATGAATA TTTCGAAAGT GGTTCATTAG AAACTGATGA            180
TAAACGAATT TACATTGTTT TTGAATATAT TGATGGTTTA ACATTGCGTG AATATCTTGA            240
TGAATTTAAA ACAGTTACTT ATGTTAAAGC TGTGAATATC GTCAGGTGCT                       290

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:9:

ACTAAATTTA TTGTTGTTAA                                                         20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:10:

CAATGTAAAT TCGTTTATCA                                                         20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:11:

TCGAACGAAG CCTTTTAGGC                                                         20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:12:

CCAAAAGCGT CGCAAACGCG                                                      20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:13:

TACAGTTTTT GATACAGCTA                                                      20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:14:

CAGTGATAGT CCAAGTTGGC                                                    20

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:15:

TGTAGTGATC ATATCAGAGT G                                                21

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:16:

GACCTATTTT ACTTGCGCTA T                                                21